US012422439B2

(12) United States Patent
Spanuth

(10) Patent No.: US 12,422,439 B2
(45) Date of Patent: Sep. 23, 2025

(54) USE OF sCD14 OR ITS FRAGMENTS OR DERIVATIVES FOR RISK STRATIFICATION, DIAGNOSIS AND PROGNOSIS

(71) Applicant: PHC Corporation, Ehime (JP)

(72) Inventor: Eberhard Spanuth, Dossenheim (DE)

(73) Assignee: PHC CORPORATION, Ehime (JP)

( * ) Notice: Subject to any disclaimer, the term of this patent is extended or adjusted under 35 U.S.C. 154(b) by 231 days.

(21) Appl. No.: 16/384,170

(22) Filed: Apr. 15, 2019

(65) Prior Publication Data

US 2019/0257841 A1    Aug. 22, 2019

Related U.S. Application Data

(63) Continuation of application No. 14/655,803, filed as application No. PCT/EP2013/078062 on Dec. 27, 2013, now abandoned.

(30) Foreign Application Priority Data

Dec. 28, 2012    (EP) .................................... 12199701

(51) Int. Cl.
    *G01N 33/68*    (2006.01)

(52) U.S. Cl.
    CPC ..... *G01N 33/6893* (2013.01); *G01N 33/6872* (2013.01); *G01N 2333/70596* (2013.01); *G01N 2800/32* (2013.01); *G01N 2800/323* (2013.01); *G01N 2800/324* (2013.01); *G01N 2800/325* (2013.01); *G01N 2800/50* (2013.01); *G01N 2800/52* (2013.01); *G01N 2800/56* (2013.01)

(58) Field of Classification Search
    CPC ........... G01N 33/6893; G01N 33/6872; G01N 2800/32; G01N 2800/56; G01N 2800/323; G01N 2800/50; G01N 2800/325; G01N 2800/324; G01N 2333/70596; G01N 2800/52; A61P 9/10; A61P 9/00
    See application file for complete search history.

(56) References Cited

U.S. PATENT DOCUMENTS

| | | | | |
|---|---|---|---|---|
| 5,003,061 A * | 3/1991 | Carobbi | .................... | C07H 3/04 536/127 |
| 9,297,802 B2 | 3/2016 | Shirakawa | | |
| 2005/0180962 A1* | 8/2005 | Raz | ...................... | A61K 31/519 424/464 |
| 2006/0068445 A1 | 3/2006 | Furusako | | |
| 2009/0120430 A1* | 5/2009 | Cipolletti | ................ | C13B 30/12 127/56 |
| 2011/0086381 A1* | 4/2011 | Naito | ................. | C07K 16/2896 530/395 |
| 2012/0114701 A1* | 5/2012 | Petit | ........................ | A61P 11/00 424/282.1 |
| 2013/0288276 A1 | 10/2013 | Matsuya et al. | | |
| 2014/0171359 A1 | 6/2014 | Shirakawa | | |
| 2015/0346217 A1* | 12/2015 | Spanuth | .................... | A61P 9/10 506/9 |

FOREIGN PATENT DOCUMENTS

| | | | | |
|---|---|---|---|---|
| CA | 2836562 A1 * | 11/2012 | ............. | A61K 45/00 |
| CN | 102590491 A | 7/2012 | | |
| EP | 1746104 A1 | 1/2007 | | |
| EP | 2530468 A1 | 12/2012 | | |
| JP | 2005106694 A | 4/2005 | | |
| JP | 2006-515294 A | 5/2006 | | |
| JP | 4040666 B2 | 11/2007 | | |
| JP | WO2009142303 * | 9/2009 | ............. | G01N 33/68 |
| JP | 201452387 A | 3/2014 | | |
| TW | 201323879 A | 6/2013 | | |
| WO | 2011017030 A2 | 2/2011 | | |
| WO | 2012096245 A1 | 7/2012 | | |
| WO | WO-2012157751 A1 * | 11/2012 | ........... | A61K 31/407 |
| WO | WO-2014104305 A1 * | 7/2014 | ......... | G01N 33/6872 |

OTHER PUBLICATIONS

Peschel et al., (The European Journal of Heart Failure 5 (2003) 609-614).*
Grunwald et al (IBL Germany, Journal of Immunological methods 1992; vol. 155, p. 225-232.*
Stelter et al (Chem. Immunol Basel Karger, 2000, vol. 74, pp. 25-41).*
E. A. Padlan, Adv Prot Chem 49:57-133; 1996.*
Corada et al., Blood, 2001; 97:1679-84.*
Yaegashi et al (J Infect Chemother 2005, 11:234-238).*
Cabell et al (Circulation 2003, 107:e185-e1870.*
Yaegashi J Infect Chemother 2005, 11:234-238.*
Mesenteric Vascular Disease (Frankel Cardiovascular Center, 1995; retrieved from https://www.umcvc.org/conditions-treatments/mesenteric-vascular-disease#:~:text=Mesenteric%20vascular%20disease%20is%20a,blood%20supply%20to%20the%20intestines.*
Shozushima J Infect Chemother (2011) 17:764-769.*
Mayeux et al. ("Biomarkers: Potential uses and Limitations"; NeuroRx (2004); vol. 1, pp. 182-188.*
English Translation for WO 2012157751 (Year: 2012).*
English translation for WO 2014104305 (Year: 2014).*
Spanuth, et al; "Presepsin (soluble CD14 subtype) as a new sepsis marker: first results of the diagnostic and prognostic validity," INFECTIONSEP 2011, vol. 39, No. 2, Sep. 1, 2011, p. S113.

(Continued)

*Primary Examiner* — Changhwa J Cheu
(74) *Attorney, Agent, or Firm* — Heslin Rothenberg Farley & Mesiti P.C.

(57) ABSTRACT

The present invention relates to a method for diagnosis of a cardiovascular disease or condition or atherosclerosis and for a method for evaluating the risk of a subject of developing the same. Methods are further provided for evaluating a subject's risk of mortality, for evaluating whether a subject will benefit from a certain treatment or whether a subject needs to be hospitalized or whether a subject may be discharged. The present invention provides sCD14 or a fragment or derivative thereof (including in particular sCD14-ST) as a novel marker for cardiovascular risk in general, more specifically as a marker for cardiovascular disease or condition, or atherosclerosis.

4 Claims, 20 Drawing Sheets

Specification includes a Sequence Listing.

(56) References Cited

OTHER PUBLICATIONS

Reiner, et al; "Soluble CD14 Genomewide Association Analysis and Relationship to Cardiovascular Risk and Mortality in Older Adults," Arteriosclerosis Thrombosis and Vascular Biology, vol. 33, No. 1, Nov. 15, 2012, p. 158.
Rauchhaus et al; "Plasma cytokine parameters and mortality in patients with chronic heart failure," Circulation, vol. 102, No. 25, Dec. 19, 2000, pp. 3060-3067, Baltimore, US.
Morange et al; "TLR4/Asp299Gly, CD14/C-260T, plasma levels of the soluble receptor CD14 and the risk of coronary heart disease: The PRIME Study," European Journal of Human Genetics, vol. 12, No. 12, Dec. 1, 2004, pp. 1041-1049.
Stoll et al; "Potential role of endotoxin as a proinflammatory mediator of atherosclerosis," Ateriosclerosis, Thrombosis, and Vascular Biology, vol. 24, No. 12, Dec. 1, 2004, pp. 2227-2236, Philadelphia, PA.
Glogowska-Ligus et al; "DNA microarray study of genes differentiating acute myocardial infarction patients from healthy person," Biomarkers, vol. 17, No. 4, Jun. 2012, pp. 379-383.
International Search Report for PCT/EP2013/078062 dated Feb. 24, 2014.
Hua, et al., "Clinical Observation and Nursing of Lactulose in Treatment of Heptic Encephalopathy", Journal of Practical Nursing, vol. 18, No. 3, Total No. 207, pp. 14-15, Mar. 2002.
Zhu, et al., "The Changes and Their Clinical Significance of Soluble CD14 and Hypersensitive C-Reactive Protein in Patients with Coronary Heart Disease," ACTA Academiae Medicinae QuingDao Universitatis, China Academic Journal Electronic Publishing House, vol. 44, No. 2, pp. 156-157 and 161, Apr. 2008.
Zhou, et al., "Research Progress of Functional Probiotic Lactic Acid Bacteria", Nat. Prod. Res. Dev., pp. 990-997 (2012).
Written Opinion of the International Searching Authority for PCT/EP2013/078062 dated Jun. 30, 2015.
Grunwald et al (IBL Germany, J Immunol Methods 1992; vol. 155, p. 225-232).
Stetler et al (Chem Immunol Basel Karger, 2000, vol. 74, pp. 25-41).
Shozushima et al (J Infect Chemother (2011) 17:764-769).
Wigand et al. Clin Exp Immunol 1994; 96:15-19.
Takeshita et al Clin Exp Immunol 2000; 119:376-381.
Juan et al., J. Biol. Chem., 1995, v. 270:1382-1387, Soluble CD14 Truncated at Amino Acid 152 Binds Lipopolysaccharide (LPS) and enables Cellular Responses to LPS.
Kobayashi et al., "Prediction of Presepsin Concentrations Through Commensurate Decline in Kidney Function in the Elderly", Clinica Chimica Acta, vol. 500, pp. 1-9. 2020.
Miyoshi et al., "Evaluation of Presepsin Levels in Patients with Chronic Kidney Disease", http://convention.jtbcom.co.jp/67jamt/, 2 pages. May 12, 2018.
Miyoshi et al., "Usefulness of Presepsin/Creatinine Ratio as a New Index That Corrects for Renal Function", The Journal of Medical Investigation, vol. 68, pp. 105-111. 2021.
Nagata et al., "Clinical Impact of Kidney Function on Presepsin Levels", PLOS ONE, pp. 1-10. Jun. 1, 2015.
Vanden Heuvel, "CD14: A Candidate Biomarker for the Prognosis of Polycystic Kidney Disease", Kidney International, vol. 78, pp. 537-538. 2010.
Choi et al., "Potential Urine Proteomics Biomarkers for Primary Nephrotic Syndrome", Clinical Proteomics, vol. 14, No. 18, 9 pages. 2017.
Morell et al., "Immune-Related Urine Biomarkers for the Diagnosis of Lupus Nephritis", The International Journal of Molecular Sciences, vol. 22, No. 7143, 18 pages. 2021.
Extended European Search Report in European Application No. 22833276.3, 14 pages. Jun. 12, 2025.

\* cited by examiner

Cutoff = 371 pg/ml, AUC = 0.957

A

B

SEQUENCE LISTING

<160> NUMBER OF SEQ ID NOS: 1

<210> SEQ ID NO 1
<211> LENGTH: 356
<212> TYPE: PRT
<213> ORGANISM: Homo sapiens

<400> SEQUENCE: 1

```
Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
            20                  25                  30

Val Ser Ala Val Glu Val Glu Ile His Ala Gly Gly Leu Asn Leu Glu
        35                  40                  45

Pro Phe Leu Lys Arg Val Asp Ala Asp Ala Asp Pro Arg Gln Tyr Ala
    50                  55                  60

Asp Thr Val Lys Ala Leu Arg Val Arg Arg Leu Thr Val Gly Ala Ala
65                  70                  75                  80

Gln Val Pro Ala Gln Leu Leu Val Gly Ala Leu Arg Val Leu Ala Tyr
                85                  90                  95

Ser Arg Leu Lys Glu Leu Thr Leu Glu Asp Leu Lys Ile Thr Gly Thr
            100                 105                 110

Met Pro Pro Leu Pro Leu Glu Ala Thr Gly Leu Ala Leu Ser Ser Leu
        115                 120                 125

Arg Leu Arg Asn Val Ser Trp Ala Thr Gly Arg Ser Trp Leu Ala Glu
    130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
```

-continued

```
            180                 185                 190
Leu Met Ala Ala Leu Cys Pro His Lys Phe Pro Ala Ile Gln Asn Leu
        195                 200             205

Ala Leu Arg Asn Thr Gly Met Glu Thr Pro Thr Gly Val Cys Ala Ala
    210                 215             220

Leu Ala Ala Ala Gly Val Gln Pro His Ser Leu Asp Leu Ser His Asn
225                 230             235                     240

Ser Leu Arg Ala Thr Val Asn Pro Ser Ala Pro Arg Cys Met Trp Ser
            245                 250             255

Ser Ala Leu Asn Ser Leu Asn Leu Ser Phe Ala Gly Leu Glu Gln Val
            260                 265             270

Pro Lys Gly Leu Pro Ala Lys Leu Arg Val Leu Asp Leu Ser Cys Asn
        275                 280             285

Arg Leu Asn Arg Ala Pro Gln Pro Asp Glu Leu Pro Glu Val Asp Asn
    290                 295             300

Leu Thr Leu Asp Gly Asn Pro Phe Leu Val Pro Gly Thr Ala Leu Pro
305                 310             315                     320

His Glu Gly Ser Met Asn Ser Gly Val Val Pro Ala Cys Ala Arg Ser
            325                 330             335

Thr Leu Ser Val Gly Val Ser Gly Thr Leu Val Leu Leu Gln Gly Ala
            340                 345             350

Arg Gly Phe Ala
        355
```

USE OF sCD14 OR ITS FRAGMENTS OR DERIVATIVES FOR RISK STRATIFICATION, DIAGNOSIS AND PROGNOSIS

CROSS REFERENCE TO RELATED APPLICATION

This application is a Continuation of U.S. Non-Provisional Patent Application, which was filed on Jun. 26, 2015 as a National Phase filing under 35 U.S.C. § 371 of PCT International Application No. PCT/EP2013/078062, filed Dec. 27, 2013, and published in English as WO 2014/102333 A1 on Jul. 3, 2014, which claims priority to European Patent Application No. 12199701.9, filed Dec. 28, 2012. The contents of each of the prior applications are incorporated by reference herein in their entirety.

SEQUENCE LISTING

The instant application contains a Sequence Listing, created on Apr. 15, 2019; the file, in ASCII format, is designated H1446506.txt and is 3.4 KB in size. The file is hereby incorporated by reference in its entirety into the instant application. The sequence listing submitted herewith is identical to the sequence listing forming part of the aforementioned international application.

FIELD OF THE INVENTION

The present invention relates to the field of means for assessing a diagnosis or a prognosis with respect to cardiovascular diseases or conditions or atherosclerosis, and to methods for evaluating the cardiovascular or atherosclerotic risk of a subject.

More specifically, the present invention relates to novel methods for diagnosing a cardiovascular disease or condition or atherosclerosis. sCD14, sCD14-ST, or a fragment or derivative of sCD14 other than sCD14-ST is provided as a novel marker for diagnosis of cardiovascular diseases or conditions or atherosclerosis. The present invention further comprises a method for the evaluation of a subject's risk of developing a future cardiovascular disease or condition or atherosclerosis. Furthermore, methods are provided for the diagnosis of an acute cardiac event in subjects showing signs of a cardiovascular disease or condition or atherosclerosis. Preferably, the method according to the present invention permits identifying if a subject is to be admitted to the hospital or an intensive care unit or if the subject can be discharged. The methods of the present invention can further be employed to discriminate between various cardiovascular diseases or conditions. Also encompassed by the present invention are devices and kits for carrying out the aforementioned methods.

BACKGROUND OF THE INVENTION

When a subject presents to an emergency department with any kind of discomfort, a rapid diagnosis of the pathological state of the subject is mandatory in order to identify the cause underlying his discomfort and avoid consequences to the subject's health. A highly relevant topic is the decision if the patient will be admitted to the hospital—for further, time consuming analysis and/or intensive care treatment—or if the patient can be discharged to home.

For example, in the case of acute cardiovascular events, a decision for a certain treatment regimen must be made, usually, within a short period of time. Cardiovascular diseases, particularly heart diseases, are the leading cause of morbidity and mortality in the Western hemisphere. Cardiovascular diseases can remain asymptomatic for long periods of time. However, they may have severe consequences once an acute cardiovascular event, such as myocardial infarction (MI) or acute decompensated heart failure (ADHF), occurs. Therefore, guidelines exist for the rapid diagnosis of patients presenting to a physician, generally in an emergency room, and being suspected of suffering from an acute coronary syndrome (ACS) (i.e. unstable angina pectoris (UAP) or myocardial infarction (MI)) or acute decompensated heart failure (ADHF, see J. Am. Coll. Cardiol. 2000; 36, pages 959-969). In a subject suspected to have acute MI, an electrocardiogram is recorded, and the level of troponin T or troponin I (cTn) is determined. Further, it is analysed if the suspected subject shows evident syndromes like chest pain, dyspnea, palpitations, nausea, vomiting and further syndromes known to the person skilled in the art. If the subject is positive in 2 of the 3 criteria, then he or she is admitted to the hospital for further examination. In a subject suspected to have ADHF, determination of plasma BNP or NT-proBNP concentration is recommended in patients being evaluated for dyspnea who have signs or symptoms compatible with heart failure, see J Card Fail 2010; 16(6): pages e134-155.

However, the composition of the subjects presenting to an emergency room is heterogeneous, comprising approximately 50% of subjects suffering from cardiovascular diseases or conditions (including both acute, i.e. ischemic conditions and non-ischemic conditions), 10% of subjects suffering from pulmonary complications and 40% subjects suffering from other complications, e.g. tumors, and which may additionally suffer from cardiovascular diseases or conditions. The conventional diagnostic techniques, specifically for emergency situations, usually do not allow for a reliable diagnosis and/or risk assessment covering these various pathological states. Further drawbacks are the lack of sufficient personnel for carrying out sophisticated diagnostic techniques and assays and the varying occupancy in emergency rooms.

At present, there does not exist a standardized diagnostic procedure covering the various cardiovascular diseases and conditions a physician may encounter in an emergency department. Thus, a rapid and accurate diagnosis of cardiovascular diseases or conditions allowing a decision if the subject can be discharged (rule-out) or has to be admitted to the hospital (rule-in) for further examination or intensive care treatment (which can be live saving) cannot be performed in the emergency department with sufficient accuracy. As a consequence thereof, many patients will either be wrongly admitted or wrongly discharged.

In some cases, so-called molecular markers permit to establish rapid and sufficiently accurate diagnosis of the pathological state of a subject. A prominent example is cTn for the diagnosis of acute MI, as mentioned beforehand, or natriuretic peptides, in particular BNP and NT-proBNP for various non-ischemic heart diseases, e.g. heart failure. Blood levels of cTn are sensitive and specific markers of myocardial necrosis that are routinely used for the diagnosis of acute MI. With regard for the determination of cTn, as an example of an ischemic marker, reference is made to Katus et al. (Mol Cell Cardiol 1989; 21:1349-53), Hamm et al. (NEJM 1992; 327: 146-50), Ohmann et al. (NEJM 1996; 335: 1333-34), Christenson et al. (Clin Chem 1998; 44: 494-501), and to EP-A-0 394 819. Although new generations of high-sensitivity cTn tests have been introduced a lack of diagnostic sensitivity and specificity in the diagnosis of myocardial infarction is still remaining especially in symptomatic patients presenting to the emergency room, see Apple and Christenson (Clin Chem 2012; 58: 54-61); and Thygesen et al. (JACC 2012, 60(16):1581-98).

A study asserted that there is a correlation between sCD14 levels and cardiovascular risk in older adults (Reiner A P et al.: Soluble CD14: Genomewide Association Analysis and Relationship to Cardiovascular Risk and Mortality in Older Adults. Arterioscler Thromb Vasc Biol; published online Nov. 15, 2012). Another study in middle-aged men, however, indicates that there is no correlation between sCD14 and subjects having coronary heart disease (Morange P E et al.: TLR4/Asp299Gly, CD14/C-260T, plasma levels of the soluble receptor CD14 and the risk of coronary heart disease: The PRIME Study. Eur J Hum Genet. 2004; 12:1041-1049).

Therefore, there is a need for diagnostic or prognostic measures, which allow an assessment and/or individual risk stratification especially for a subject presenting early after onset of symptoms to the emergency department. The measures should permit this assessment/risk stratification also in subjects that have not previously been diagnosed with cardiovascular diseases or conditions, in particular not with acute cardiovascular diseases.

The technical problem underlying the present invention can be seen as the provision of means and methods for complying with the aforementioned needs.

The technical problem is solved by the embodiments characterized in the claims and herein below.

SUMMARY OF THE INVENTION

The present invention provides the following aspects, subject-matters and preferred embodiments, which respectively taken alone or in combination, further contribute to solving the object of the present invention:

1. A method for evaluating a subject's risk of developing a cardiovascular disease or condition or atherosclerosis, comprising the steps of
   a) determining the amount of a compound selected from sCD14, sCD14-ST, or a fragment or derivative of sCD14 other than sCD14-ST, in a sample of said subject,
   b) comparing the amount determined in step a) to at least one reference amount, and
   c) evaluating the subject's individual risk of developing a cardiovascular disease or condition based on the result obtained in step b).

2. A method for diagnosing a cardiovascular disease or condition or atherosclerosis in a subject, comprising
   a) determining of the amount of a compound selected from sCD14, sCD14-ST, or a fragment or derivative of sCD14 other than sCD14-ST, in a sample of said subject,
   b) comparing the amount determined in step a) to at least one reference amount, and
   c) determining the presence or absence of the cardiovascular disease or condition based on the result obtained in step b).

3. A method for evaluating the risk of mortality in a subject with a cardiovascular disease or condition or atherosclerosis, comprising
   a) determining the amount of a compound selected from sCD14, sCD14-ST, or a fragment or derivative of sCD14 other than sCD14-ST, in a sample of said subject,
   b) comparing the amount determined in step a) to at least one reference amount, and
   c) determining the subject's risk of mortality based on the result obtained in step b).

4. A method for evaluating whether a subject with a cardiovascular disease or condition or atherosclerosis will benefit from the treatment with substance selected from the group consisting of antibiotics, probiotics and lactulose, comprising the steps of
   a) determining of the amount of a compound selected from sCD14, sCD14-ST, or a fragment or derivative of sCD14 other than sCD14-ST, in a sample of said subject,
   b) comparing the amount determined in step a) to at least one reference amount, and
   c) evaluating said likelihood based on the result obtained in step b).

5. A method for determining whether a subject needs to be hospitalized due to a cardiovascular disease or condition or atherosclerosis, the method comprising
   a) determining the amount of a compound selected from sCD14, sCD14-ST, or a fragment or derivative of sCD14 other than sCD14-ST, in a sample of said subject,
   b) comparing the amount determined in step a) to at least one reference amount, and
   c) determining whether the subject needs to be hospitalized on the result obtained in step b).

6. The method according to any of items 1 to 5, further comprising the steps of
   a') determining in the same or different sample of the same individual at least one additional marker,
   b') comparing the amount of the at least one additional marker determined in step a') to at least one reference amount of said additional marker, and
   c') performing the respective step c) by combining the result obtained for said compound in step b) and the result obtained in step b') for the at least one additional marker.

7. The method according to item 6, wherein step c') comprises evaluating the subject's individual risk of developing a cardiovascular disease or condition or atherosclerosis by combining the results obtained in step b) for said compound and for said at least one additional marker, respectively.

8. The method according to item 6, wherein step c') comprises determining the presence or absence of the cardiovascular disease or condition or atherosclerosis by combining the results obtained in step b) for said compound and for said at least one additional marker, respectively.

9. The method according to item 6, wherein step c') comprises determining the subject's risk of mortality by combining the results obtained in step b) for said compound and for said at least one additional marker, respectively.

10. The method according to item 6, wherein step c') comprises determining whether a subject will benefit from the treatment with a substance selected from the group consisting of antibiotics, probiotics and lactulose by combining the results obtained in step b) for said compound and for said at least one additional marker, respectively.

11. The method according to item 6, wherein step c') comprises determining whether a subject needs to be hospitalized by combining the results obtained in step b) for said compound and for said at least one additional marker, respectively.

12. The method according to item 4 or 6, wherein the antibiotic is not resorbed by the gut.

13. The method according to any of items 4, 6 or 12, wherein the antibiotic is an aminoglycoside.

14. The method according to any of items 4, 6, 12 or 13, wherein the antibiotic is neomycin or paromycin.

15. The method according to any of items 4, 6 or 12 to 14, wherein the subject has a cardiovascular disease or condition, preferably acute heart failure.

16. The method according to item 6, wherein step c') comprises determining whether a subject needs to be hospitalized by combining the results obtained in step b) for said compound and for said at least one additional marker, respectively.

17. The method according to any of items 6 to 16, wherein the at least one additional marker is selected from the group consisting of neurohormonal markers, regulators of water balance, ischemic cardiac markers, cytokines, inflammatory markers and cellular adhesion molecules.

18. The method according to any of items 6 to 17, preferably wherein the at least one additional marker is selected from the group consisting of procalcitonin, C-reactive protein, copeptin, and markers of the transforming growth factor-β cytokine superfamily, and/or the group consisting of a neurohormonal marker, an ischemic cardiac marker; an inflammatory marker and optionally a marker of the interleukin-1 receptor family.

19. The method according to any of items 1 to 18, wherein the subject shows symptoms of one or more cardiovascular diseases or conditions selected from the group consisting of acute coronary syndrome, acute heart failure, chronic heart failure, coronary artery disease, angina pectoris, myocardial infarction, ischemic stroke, hemorrhagic stroke and transient ischemic attacks.

20. The method according to any of items 1 to 19, wherein the method is for diagnosing chronic heart failure, preferably wherein the amount of said compound (preferably sCD14-ST) is 115 pg/ml or higher, more preferably 150 pg/ml or higher, even more preferably 260 pg/ml or higher.

21. The method according to any of items 1 to 19, wherein the method is for diagnosing chronic heart failure, preferably wherein the amount of said compound (preferably sCD14-ST) is between 115 pg/ml and 4000 pg/ml, more preferably between 150 pg/ml and 3000 pg/ml, even more preferably between 260 pg/ml and 2000 pg/ml.

22. The method according to any of items 1 to 19, wherein the method is for diagnosing unstable angina pectoris, preferably wherein the amount of said compound (preferably sCD14-ST) is 214 pg/ml or higher, more preferably 216 pg/ml or higher, even more preferably 222 pg/ml or higher.

23. The method according to any of items 1 to 19, wherein the method is for diagnosing unstable angina pectoris, preferably wherein the amount of said compound (preferably sCD14-ST) is between 214 pg/ml and 4000 pg/ml, more preferably between 216 pg/ml and 3000 pg/ml, even more preferably between 222 pg/ml and 2000 pg/ml.

24. The method according to any of items 1 to 19, wherein the method is for diagnosing acute heart failure, preferably wherein the amount of said compound (preferably sCD14-ST) is 295 pg/ml or higher, more preferably 354 pg/ml or higher, even more preferably 455 pg/ml or higher.

25. The method according to any of items 1 to 19, wherein the method is for diagnosing acute heart failure, preferably wherein the amount of said compound (preferably sCD14-ST) is between 295 pg/ml and 4000 pg/ml, more preferably between 354 pg/ml and 3000 pg/ml, even more preferably between 455 pg/ml and 2000 pg/ml.

26. The method according to any of items 1 to 19, 24 or 25, wherein the method is for diagnosing acute decompensated heart failure (ADHF).

27. The method according to any of items 1 to 19, wherein the method is for diagnosing myocardial infarction, preferably wherein the amount of sCD14-ST is 260 pg/ml or higher, more preferably 276 pg/ml or higher, even more preferably 295 pg/ml or higher.

28. The method according to any of items 1 to 19, wherein the method is for diagnosing myocardial infarction, preferably wherein the amount of said compound (preferably sCD14-ST) is between 260 pg/ml and 4000 pg/ml, more preferably between 276 pg/ml and 3000 pg/ml, even more preferably between 295 pg/ml and 2000 pg/ml.

29. The method according to any of items 1 to 19, 27 or 28, wherein the method is for diagnosing non-ST-elevated myocardial infarction.

30. The method according to any of items 1 to 19, wherein the method is for discriminating between chronic heart failure and acute heart failure, wherein preferably the amount of said compound (preferably sCD14-ST) in a sample from a subject having acute heart failure is 340 pg/ml or higher, more preferably 354 pg/ml or higher, even more preferably 455 pg/ml or higher.

31. The method according to any of items 1 to 19, wherein the method is for identifying a subject having a cardiovascular disease or condition or atherosclerosis that has an elevated risk of mortality, preferably wherein the amount of said compound (preferably sCD14-ST) is 500 pg/ml or higher, more preferably 800 pg/ml or higher, even more preferably 1300 pg/ml.

32. The method according to any of items 1 to 19, wherein the method is for identifying subjects having a cardiovascular disease or condition or atherosclerosis that have an elevated risk of mortality, preferably wherein the amount of said compound (preferably sCD14-ST) is between 500 pg/ml and 4000 pg/ml, more preferably between 800 pg/ml and 3000 pg/ml, even more preferably between 1300 pg/ml and 2000 pg/ml.

33. The method according to any of items 1 to 19, 31 or 32, wherein the method is for identifying a subgroup of subjects having acute heart failure with an elevated risk of mortality.

34. The method according to any of items 1 to 33, wherein the method is for assessing a prognosis of a subject with a cardiovascular disease or condition or atherosclerosis.

35. The method according to any of items 1 to 19, wherein the method is for evaluating the risk of a subject free from clinical signs of cardiovascular diseases or conditions or atherosclerosis to develop a cardiovascular disease or condition or atherosclerosis.

36. The method according to item 35, wherein the subject has an elevated risk of developing a cardiovascular disease or condition or atherosclerosis if an amount of said compound (preferably sCD14-ST) determined in a sample from a subject is preferably 225 pg/ml or higher, more preferably 240 pg/ml or higher, even more preferably 260 pg/ml or higher.

37. The method according to any of items 1 to 36, wherein the reference amount of said compound (preferably sCD14-ST) in healthy subjects is preferably between 223 pg/ml and 262 pg/ml.

38. The method according to any of items 1 to 37, wherein the sample is a blood sample.

39. The method according to item 38, wherein the sample is a sample, which has been isolated from a subject.

40. The method according to any of items 1 to 39, which is carried out in vitro.

41. The method according to any of items 1 to 40, in which determining the amount of said compound and/or the amount of the at least one additional marker comprises the steps of (i) contacting the peptide with a specific ligand, (ii) (optionally) removing non-bound ligand, (iii) measuring the amount of bound ligand.

42. The method according to any of items 1 to 41, wherein the amount of said compound and/or the amount of the at least one additional marker is determined by an immunoassay.

43. The method according to any of items 1 to 42, wherein said compound is sCD14-ST and the amount of sCD14-ST is determined using an antibody specific for sCD14-ST.

44. The method according to item 43, wherein the antibody specific for sCD14-ST does not bind to sCD14.

45. The method according to any of items 1 to 44, wherein the comparison in step b) or b'), respectively, is computer-assisted.

46. The method according to item 45, wherein the values of the determined amounts of said compound, sCD14-ST and/or the at least one additional marker are compared to the values corresponding to the respective reference amounts by a computer program.

47. The method according to item 46, wherein the computer program evaluates the result of the comparison and provides the result of the evaluation in a suitable output format.

48. Use of a compound selected from sCD14, sCD14-ST, or a fragment or derivative of sCD14 other than sCD14-ST, as a marker for cardiovascular diseases or conditions or atherosclerosis.

49. A use according to item 48, wherein the cardiovascular disease or condition is selected from the group consisting of acute coronary syndrome, acute heart failure, chronic heart failure, coronary artery disease, angina pectoris, myocardial infarction, ischemic stroke, hemorrhagic stroke, transient ischemic attacks and pulmonary embolism.

50. A use according to item 48 or 49, wherein the marker is used in an in vitro assay.

51. A substance selected from the group consisting of antibiotics, probiotics and lactulose for use in the treatment of a subject with a cardiovascular disease or condition or atherosclerosis and having an increased plasma level of a compound selected from sCD14, sCD14-ST, or a fragment or derivative of sCD14 other than sCD14-ST.

52. A substance for use according to item 51, wherein the antibiotic is not resorbed by the gut.

53. A substance for use according to item 51 or 52, wherein the antibiotic is an aminoglycoside.

54. A substance for use according to any of items 51 to 53, wherein the antibiotic is neomycin or paromycin.

55. A substance for use according to any of items 51 to 54, which is not for use in a treatment of sepsis or a disease associated with phagocyte dysfunction such as uremia, decrease in the activity of serum opsonin, complement deficiency, congenital phagocytosis dysfunction, chronic granulomatous disease, myeloperoxidase defect, leukemia, malignant lymphoma, bacterial endocarditis, diabetes and hepatic cirrhosis.

56. A substance for use according to any of items 51 to 55, wherein the increased plasma level is 345 pg/ml or higher, preferably 800 pg/ml or higher, more preferably 1300 pg/ml or higher.

57. A kit for diagnosis of a cardiovascular disease or condition or atherosclerosis, for evaluating a subject's risk of developing a cardiovascular disease or condition or atherosclerosis, for evaluating a risk of mortality in a subject with a cardiovascular disease or condition or atherosclerosis, for evaluating the likelihood that a subject with a cardiovascular disease or condition or atherosclerosis will benefit from the treatment with a substance selected from the group consisting of antibiotics, probiotics and lactulose and/or for evaluating whether a subject needs to be hospitalized due to a cardiovascular disease or condition or atherosclerosis, the kit comprising
  a) means for determining the amount of sCD14-ST in a sample from a subject;
  b) instructions for the diagnosis and/or risk evaluation based on the amount of sCD14-ST determined by a); and optionally
  c) means for determining the amount of at least one additional marker and instructions for the diagnosis and/or risk evaluation based on the determined amount of said at least one additional marker.

58. A method according to any one of items 1-47, wherein said risk of mortality is the risk of mortality after cardiac surgery or the subject has undergone cardiac surgery.

59. A method according to item 3, wherein said risk of mortality is the risk of mortality after cardiac surgery or the subject has undergone cardiac surgery.

60. The use of a compound selected from sCD14, sCD14-ST, or a fragment or derivative of sCD14 other than sCD14-ST, as a marker for evaluating the risk of mortality in a subject after cardiac surgery.

61. A method for differentiating between cardiac and non-cardiac chest pain in a subject presenting with chest pain, comprising the steps of
  a) determining the amount of a compound selected from sCD14, sCD14-ST, or a fragment or derivative of sCD14 other than sCD14-ST, in a sample of said subject,
  b) comparing the amount determined in step a) to at least one reference amount, and
  c) determining the presence or absence of cardiac chest pain based upon the result obtained in step (b).

62. The use of a compound selected from sCD14, sCD14-ST, or a fragment or derivative of sCD14 other than sCD14-ST as a marker for differentiating between cardiac and non-cardiac chest pain.

DETAILED DESCRIPTION OF THE INVENTION

Figure 1:
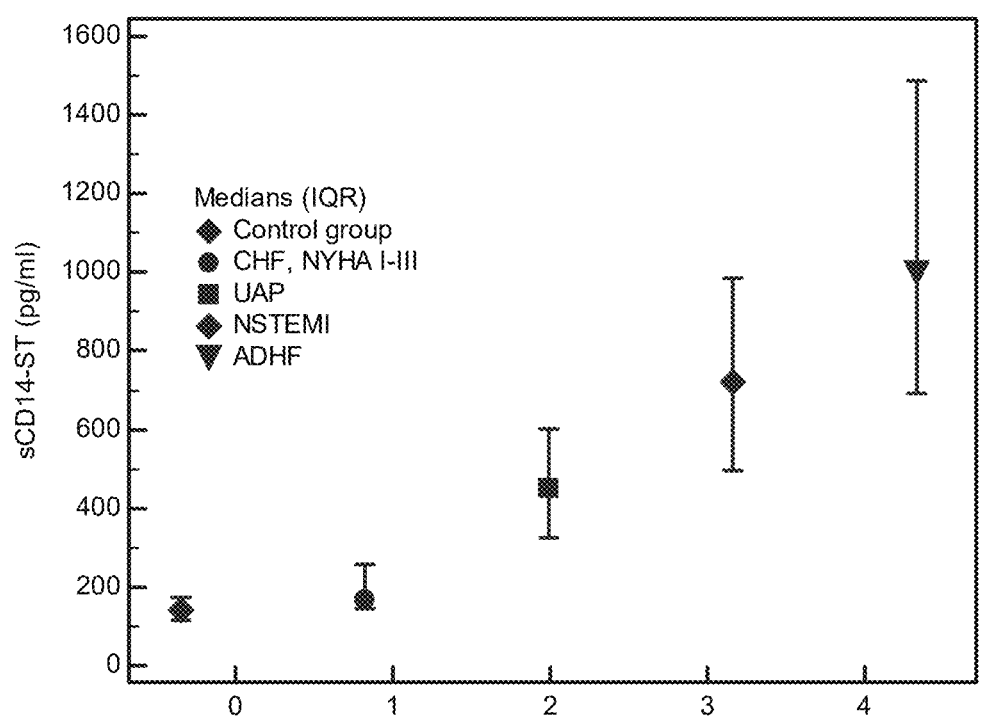
FIG. 1: sCD14-ST plasma concentration in the healthy control group and different subject groups.

The present invention is now described in more detail by preferred embodiments and examples, which are however presented for illustrative purpose only and shall not be understood as limiting the scope of the present invention in any way.

The present invention is based on the unexpected finding that sCD14-ST is elevated in subjects having a cardiovascular disease or condition or atherosclerosis as well as in subjects that are free from any clinical signs of cardiovascular disease or atherosclerosis but have an elevated risk of developing a cardiovascular disease or condition or atherosclerosis.

sCD14-ST has previously been used as marker for applications altogether unrelated to the field of cardiovascular diseases or conditions or atherosclerosis. Diagnostic techniques, which are applicable to both, a standard laboratory as well as a so-called point-of-care situation, have become available for sepsis, which can readily be assessed by employing systems based on the measurement of sCD14-ST (EP 1 746 104 A1). sCD14-ST has been proposed for evaluating phagocyte function (EP 2 280 279 A1).

It has now been surprisingly found that determining a compound selected from sCD14, sCD14-ST, or a fragment or derivative of sCD14 other than sCD14-ST, and comparing it with a respective reference amount of said compound has an outstanding diagnostic power with respect to cardiovascular diseases or conditions or atherosclerosis. It has further been found that such a compound can be used for predicting cardiovascular diseases or conditions or atherosclerosis in a subject, wherein the subject may be either a subject previously diagnosed with a cardiovascular disease or condition or atherosclerosis or a subject free of any clinical signs of cardiovascular disease or atherosclerosis. Moreover, determining the levels of such a compound in a subject allows for discriminating between specific cardiovascular diseases or conditions or atherosclerosis.

In particular, the method according to the invention provides a means for diagnosis of a cardiovascular disease or condition or atherosclerosis based on the determination of the amount of a compound selected from sCD14, sCD14-ST, or a fragment or derivative of sCD14 other than sCD14-ST in a subject. Furthermore, the method according to the invention allows for evaluating a subject's risk of developing a cardiovascular disease or condition or atherosclerosis as well as for evaluating a subject's overall risk of mortality. In a preferred embodiment, the method according to the invention also provides a means for discriminating between specific cardiovascular diseases or conditions or atherosclerosis in a subject. Alternatively, the method allows for evaluating whether a subject with a cardiovascular disease or condition or atherosclerosis will benefit from the treatment with one or more substances selected from the group consisting of antibiotics, probiotics and lactulose. The method can also be employed in order to determine whether a subject needs to be hospitalized based on the amount of a compound selected from sCD14, sCD14-ST, or a fragment or derivative of sCD14 other than sCD14-ST, present in a sample from said subject.

In a preferred embodiment, the method according to the invention comprises the steps of
 a) determining the amount of a compound selected from sCD14, sCD14-ST, or a fragment or derivative of sCD14 other than sCD14-ST in a sample of a subject,
 b) comparing the amount of said compound determined in step a) to at least one reference amount, and
 c) elaborating the diagnosis or risk/benefit evaluation based on the result obtained in step b).

Specifically, the diagnosis or the evaluation as described above is independent of any other clinical sign or symptom.

It has advantageously been found that determining the amount of a compound selected from sCD14, sCD14-ST, or a fragment or derivative of sCD14 other than sCD14-ST in a subject is sufficient and provides significant benefits for diagnosing a cardiovascular disease or condition or atherosclerosis and/or for evaluating a subject's risk of developing a cardiovascular disease or condition or atherosclerosis. With respect to prior art methods (in particular measurement of cardiac troponin, cTn), the method according to the invention has the advantage that no second or further measurement is required (e.g. for determining rise and fall or any other kinetics of a marker), thus allowing for more efficient diagnoses and/or evaluations.

Moreover, the diagnostic and prognostic power of the method according to the invention is superior as compared to the state of the art. It has surprisingly been found that the method according to the invention provides for results that are characterized by outstanding sensitivity and/or specificity.

In a preferred embodiment, the method according to the invention comprises the simultaneous determination of an additional marker, selected from a neurohormonal marker, a marker, which is a regulator of water balance, an ischemic cardiac marker, a marker of the transforming growth factor-β cytokine superfamily, and/or an inflammatory marker in combination with a compound selected from sCD14, sCD14-ST, or a fragment or derivative of sCD14 other than sCD14-ST, whereafter the determined amounts are compared to reference amounts of the determined markers, respectively. According to the present invention, it has further surprisingly been found that, when an additional marker, selected from a neurohormonal marker, a marker, which is a regulator of water balance, an ischemic cardiac marker, a marker of the transforming growth factor-β cytokine superfamily, interleukin receptor family, e.g. interleukin 1 receptor-like 1, also known as IL1RL1 and ST2, or neutrophil gelatinase-associated lipocalin (NGAL), and/or an inflammatory marker, is determined in combination with a compound selected from sCD14, sCD14-ST, or a fragment or derivative of sCD14 other than sCD14-ST in the same or different sample of the subject, an even higher accuracy is achieved for diagnosing a cardiovascular disease or condition or atherosclerosis in a subject, for identifying if a subject is at elevated risk of developing a cardiovascular disease or condition or atherosclerosis or for identifying if a subject is to be admitted to the hospital or for predicting the risk of mortality for a subject. Again, such a remarkably high predictive value is achieved independently from and irrespective of other diagnoses or known disease status of the subject, even with subjects having no clinical sign or apparent symptom of a cardiovascular disease or condition or atherosclerosis.

In certain embodiments, said at least one additional marker may preferably be selected from a neurohormonal marker (e.g. NT-proBNP), an ischemic cardiac marker (e.g. hsTnT), an inflammatory marker (e.g. C-reactive protein, CRP) and a marker of the interleukin-1 receptor family (e.g. IL1RL1/ST2). In such embodiments, the disease or condition is a disease or condition within the meaning of the present invention, i.e. a cardiovascular disease or condition or atherosclerosis. It may be or include, e.g., acute heart failure. E.g., the disease or condition may also selected from the group consisting of acute coronary syndrome, acute heart failure, chronic heart failure, coronary artery disease, angina pectoris, myocardial infarction, ischemic stroke, hemorrhagic stroke, and/or transient ischemic attacks.

The term "regulator of water balance" as used herein refers to a substance, which acts on homeostatic control mechanisms in a subject in order to regulate and maintain a balance between fluid uptake and output.

The term "subject" as used herein relates to animals, preferably mammals, and, more preferably, humans.

In a preferred embodiment of the present invention, a subject shall not exhibit any symptoms of a cardiovascular disease or condition or atherosclerosis. In particular, the subject shall not be suffering from an acute cardiovascular event as defined by the American College of Cardiology, e.g. chest discomfort, dyspnea, ECG changes and others as described above. More preferably, the subject shall not exhibit one or more episodes of angina lasting at least 5 min within the preceding 24 h, and not have either a positive cTn value when conventional assays are used or at least 0-5 mm of transient or persistent ST-segment depression not known to be pre-existing and not attributable to coexisting disorders. Alternatively, the subject shall not exhibit symptoms of ischemia that were increasing or occurring at rest, or that warranted the suspicion of acute myocardial infarction, with the last episode within the preceding 48 h. Myocardial ischaemia has to be verified by electrocardiography (ST depression=0.1 mV or T-wave inversion=0.1 mV) or by raised biochemical markers (creatine kinase [CK]-MB>6 ug/L, high sensitivity troponinT>13 pg/ml, qualitative cTn test positive, or catalytic activity of CK, CK-B, or CK MB higher than the local diagnostic limit for myocardial infarction).

A "cardiovascular disease or condition" in the meaning of the present invention may be any physiological situation in a subject, which is recognized by the skilled person as an abnormal state of the subject, which is characterized by or linked to phenomena involving alterations of the cardiovascular system. Cardiovascular diseases or conditions are, for example, acute coronary syndrome (ACS), acute heart failure, acute decompensated heart failure (ADHF), chronic heart failure, coronary artery disease, angina pectoris, myocardial infarction, ischemic stroke, hemorrhagic stroke and transient ischemic attacks. ACS patients can show unstable angina pectoris (UAP) or myocardial infarction (MI). MI can be an ST-elevation MI (STEMI) or a non-ST-elevated MI (NSTEMI). The occurring of an ACS can be followed by a left ventricular dysfunction (LVD) or development of heart failure. Further preferred cardiovascular diseases or conditions encompass cardiac brady- or tachyarrhythmias including sudden cardiac death and stroke (cerebrovascular events or accidents). Most preferably, the said cardiovascular complication is ACS and ADHF.

In a preferred embodiment, the method is used in order to provide a "rule-in" or a "rule-out" diagnosis, respectively. In the meaning of the invention, "rule-in" refers to a diagnosis, which allows for positively determining the presence of a certain disease or condition in a subject. The term "rule-out", on the other hand, refers to a diagnosis, which is capable of excluding a certain disease or condition. As used herein, the term "rule-in" may also refer to a situation that requires admission to a hospital, whereas "rule-out" may refer to a situation, which allows for the subject's discharge.

The invention also provides the use of a compound selected from sCD14, sCD14-ST, or a fragment or derivative of sCD14 other than sCD14-ST as a marker for differentiating between cardiac and non-cardiac chest pain. In some embodiments, the invention thus also provides methods for differentiating between cardiac and non-cardiac chest pain in a subject presenting with chest pain.

Chest pain may, e.g., be identified as cardiac chest pain when the amount of a compound selected from sCD14, sCD14-ST, or a fragment or derivative of sCD14 other than sCD14-ST—preferably the amount of sCD14-ST—is, e.g., 200 pg/ml or higher, 210 pg/ml or higher, 220 pg/ml or higher, 230 pg/ml or higher, 240 pg/ml or higher, 250 pg/ml or higher, 255 pg/ml or higher, 300 pg/ml or higher, or 380 pg/ml or higher. Preferably, the amount of the compound is 220 pg/ml or higher, or 255 pg/ml or higher.

Chest pain may, e.g., be identified as non-cardiac chest pain when the amount of sCD14-ST does not exceed, e.g., 200 pg/ml, 210 pg/ml, 220 pg/ml, 230 pg/ml, 240 pg/ml, 250 pg/ml, 255 pg/ml, 300 pg/ml, or 380 pg/ml. Preferably, the amount of sCD14-ST does not exceed 220 pg/ml or 255 pg/ml.

Advantageously, the differentiation between cardiac and non-cardiac chest pain is performed when the subject first presents with chest pain, e.g. at the stage of admission (e.g., into an emergency room). Preferably, troponin is initially negative.

In some embodiments, a subject undergoes cardiac surgery, e.g. elective cardiac surgery, or emergency cardiac surgery. The invention provides, e.g., methods of evaluating or predicting the risk of mortality in a subject after undergoing cardiac surgery (e.g. elective cardiac surgery, or emergency cardiac surgery). The invention provides, e.g., methods of identifying a subject having an elevated risk of mortality after cardiac surgery (e.g. elective cardiac surgery, or emergency cardiac surgery). The invention thus provides the use of a compound selected from sCD14, sCD14-ST, or a fragment or derivative of sCD14 other than sCD14-ST as a marker for evaluating or predicting the risk of mortality in a subject after cardiac surgery (e.g. elective cardiac surgery, or emergency cardiac surgery).

When a subject undergoes cardiac surgery, the method may be carried out, e.g., pre-, peri-, or postoperatively. The method may be carried out within 1, 2, 3, 4 or 5 days of surgery, e.g. on the first postoperative day.

When a subject undergoes cardiac surgery, an elevated risk of mortality may be determined to be present, e.g., when the amount of a compound selected from sCD14, sCD14-ST, or a fragment or derivative of sCD14 other than sCD14-ST—preferably the amount of sCD14-ST—is, e.g., 300 pg/ml or higher, e.g., 325 pg/ml or higher, e.g., 350 pg/ml or higher, 371 pg/ml or higher, 375 pg/ml or higher, 400 pg/ml or higher, 500 pg/ml or higher, 600 pg/ml or higher, 800 pg/ml or higher, 1000 pg/ml or higher, 1300 pg/ml or higher, 1600 pg/ml or higher, or 1900 pg/ml or higher.

The term "sample" refers to a sample of a body fluid, to a sample of separated cells or to a sample from a tissue or an organ. Samples of body fluids can be obtained by well known techniques and include, preferably, samples of blood, plasma, serum or urine, more preferably, samples of blood, plasma or serum. Tissue or organ samples may be obtained from any tissue or organ by, e.g., biopsy. Separated cells may be obtained from body fluids or tissues or organs by separating techniques such as centrifugation or cell sorting. Preferably, cell-, tissue- or organ samples are obtained from those cells, tissues or organs, which express or produce the peptides referred to as markers herein.

Most preferably, the compound according to the methods and uses of the invention is sCD14-ST.

Herein, a fragment or derivative may be, e.g., a fragment or derivative of sCD14 other than sCD14-ST.

Herein, a fragment or derivative of sCD14 (e.g. sCD14-ST or a fragment or derivative other than sCD14-ST) may be defined by its specific binding to one or more antibody/antibodies that binds/bind specifically to
  an epitope located within a fragment, derivative or sequence defined herein,
  to a peptide the amino acid sequence of which comprises or consists of a fragment, derivative or sequence defined herein,
  or to one or more antibody/antibodies prepared using a peptide the amino acid sequence of which comprises or consists of a fragment, derivative or sequence defined herein.

A fragment or derivative of sCD14 (e.g. sCD14-ST or a fragment or derivative other than sCD14-ST) may bind specifically to
  an antibody that specifically binds to an epitope located within amino acids 17-26 of SEQ ID NO: 1, and/or
  an antibody that specifically binds to an epitope located within amino acids 53-68 of SEQ ID NO: 1, and/or
  an antibody that specifically binds to a peptide the amino acid sequence of which comprises or consists of amino acids 17-26 of SEQ ID NO: 1 and/or
  an antibody that specifically binds to a peptide the amino acid sequence of which comprises or consists of amino acids 53-68 of SEQ ID NO: 1, and/or
  an antibody prepared using a peptide comprising or consisting of amino acids 17-26 of SEQ ID NO: 1 and/or
  an antibody prepared using a peptide comprising or consisting of amino acids 53-68 of SEQ ID NO: 1

Herein, a fragment or derivative of sCD14 (e.g. a fragment or derivative other than sCD14-ST) may comprise, e.g., at least 10, 15, 16, 20, 30, 40, 50, 51, 52, 60, 68, 70, 80, 90, 100, 110, 120, 150 or 200 consecutive amino acids of SEQ ID NO: 1. Preferably, a fragment or derivative of sCD14 (e.g. a fragment or derivative other than sCD14-ST) comprises at least 10 consecutive amino acids of SEQ ID NO: 1. In certain preferred embodiments, a fragment or derivative may comprise at least 20 or 30 consecutive amino acids of SEQ ID NO: 1. A fragment or derivative may also comprise at least 52, 68, or e.g. 75 consecutive amino acids of SEQ ID NO: 1. A fragment or derivative may also comprise at least 90 or 100 consecutive amino acids of SEQ ID NO: 1.

In certain embodiments, a fragment or derivative comprises the N-terminal amino acid, or the N-terminal 5, 6, 7, 8, 9, 10, 11 or 12 (preferably e.g. 11) amino acids of SEQ ID NO: 1. A fragment or derivative may alternatively comprise the C-terminus or the C-terminal 5, 6, 7, 8, 9, 10, 11 or 12 (preferably e.g. 11) amino acids of SEQ ID NO: 1. In certain embodiments, a fragment or derivative comprises neither the N-terminus nor the C-terminus of SEQ ID NO: 1. In certain embodiments, the N-terminus of a fragment or derivative lies within 10, 20, 30, 40, 50, 60, 70, 80, 90, 100, 110, 150 or 200 amino acids of the N-terminus of SEQ ID NO: 1. In certain embodiments, the N-terminus of a fragment or derivative lies at least 5, 10, 20, 30, 40, 50, 60, 70, 80, 90, 100, 110, 150 or 200 amino acids from the N-terminus of SEQ ID NO: 1. In certain embodiments, the C-terminus of a fragment or derivative lies within 10, 20, 30, 40, 50, 60, 70, 80, 90, 100, 110, 150 or 200 amino acids of the C-terminus of SEQ ID NO: 1. In certain embodiments, the C-terminus of a fragment or derivative lies at least 5, 10, 20, 30, 40, 50, 60, 70, 80, 90, 100, 110, 150 or 200 amino acids from the C-terminus of SEQ ID NO: 1.

In certain embodiments, a fragment or derivative may, e.g., comprise at least 10 consecutive amino acids of SEQ ID NO: 1 and its N-terminus lies within 10, 20 or 30 amino acids of the N-terminus of SEQ ID NO: 1.

In certain embodiments, a fragment or derivative may, e.g., comprise at least 20 consecutive amino acids of SEQ ID NO: 1 and its N-terminus lies within 10, 20 or 30 amino acids of the N-terminus of SEQ ID NO: 1.

In certain embodiments, a fragment or derivative may, e.g., comprise at least 40 consecutive amino acids of SEQ ID NO: 1 and its N-terminus lies within 10, 20 or 30 amino acids of the N-terminus of SEQ ID NO: 1.

In certain embodiments, a fragment or derivative may, e.g., comprise at least 60 consecutive amino acids of SEQ ID NO: land its N-terminus lies within 10, 20 or 30 amino acids of the N-terminus of SEQ ID NO: 1.

In certain embodiments, a fragment or derivative may, e.g., comprise at least 100 consecutive amino acids of SEQ ID NO: land its N-terminus lies within 10, 20 or 30 amino acids of the N-terminus of SEQ ID NO: 1.

In other embodiments, the fragment or derivative may, e.g., comprise at least 10 consecutive amino acids of SEQ ID NO: 1and its C-terminus lies within 10, 20 or 30 amino acids of the C-terminus of SEQ ID NO: 1.

In other embodiments, a fragment or derivative may, e.g., comprise at least 20 consecutive amino acids of SEQ ID NO: 1and its C-terminus lies within 10, 20 or 30 amino acids of the C-terminus of SEQ ID NO: 1.

In other embodiments, a fragment or derivative may, e.g., comprise at least 40 consecutive amino acids of SEQ ID NO: 1and its C-terminus lies within 10, 20 or 30 amino acids of the C-terminus of SEQ ID NO: 1.

In other embodiments, a fragment or derivative may, e.g., comprise at least 60 consecutive amino acids of SEQ ID NO: 1and its C-terminus lies within 10, 20 or 30 amino acids of the C-terminus of SEQ ID NO: 1.

In other embodiments, a fragment or derivative may, e.g., comprise at least 100 consecutive amino acids of SEQ ID NO: 1and its C-terminus lies within 10, 20 or 30 amino acids of the C-terminus of SEQ ID NO: 1.

In other embodiments, e.g. the N-terminus of a fragment or derivative lies within 10 amino acids from the N-terminus of SEQ ID NO: 1 and the C-terminus of said fragment or derivative lies at least 30, 50 or 100 amino acids from the C-terminus of SEQ ID NO: 1.

In other embodiments, e.g. the N-terminus of a fragment or derivative lies within 30 amino acids from the N-terminus of SEQ ID NO: 1 and the C-terminus of said fragment or derivative lies at least 30, 50 or 100 amino acids from the C-terminus of SEQ ID NO: 1.

In other embodiments, e.g. the N-terminus of a fragment or derivative lies at least 30 amino acids from the N-terminus of SEQ ID NO: 1 and the C-terminus of said fragment or derivative lies at least 30, 50 or 100 amino acids from the C-terminus of SEQ ID NO: 1.

In certain embodiments, a fragment or derivative may comprise amino acids 1-350, 5-356, 1-10, 1-11, 1-15, 1-16, 1-17, 1-20, 1-26, 1-30, 1-40, 1-50, 1-52, 1-53, 1-60, 1-68, 1-80, 1-100, 1-120, 1-140, 1-160, 1-180, 1-200, 1-220, 1-240, 1-260, 1-280, 1-300, 1-320, 1-340, and/or 1-356 of SEQ ID NO: 1.

In certain embodiments, a fragment or derivative may comprise amino acids 17-26 and/or 53-68 of SEQ ID NO: 1, or amino acids 17-68 of SEQ ID NO: 1.

In certain embodiments herein, a fragment or derivative may, e.g., combine 2 or more properties selected from:
  having a molecular weight of 13±2 kDa as measured by electrophoresis (e.g. SDS-PAGE) under non-reducing conditions;
  comprising the amino acid sequence of positions 1-11 of SEQ ID NO: 1; and/or
  binding specifically to an antibody prepared using a peptide consisting of the amino acid sequence of positions 53-68 of SEQ ID NO: 1 (and/or to an antibody that specifically binds to an epitope located within amino acids 53-68 of SEQ ID NO: 1; and/or to an antibody that specifically binds to a peptide the amino acid sequence of which comprises or consists of amino acids 53-68 of SEQ ID NO: 1).

In other embodiments, a fragment or derivative does not have one or more properties selected from:
  having a molecular weight of 13±2 kDa as measured by electrophoresis (e.g. SDS-PAGE) under non-reducing conditions;
  comprising the amino acid sequence of positions 1-11 of SEQ ID NO: 1; and/or
  binding specifically to an antibody prepared using a peptide consisting of the amino acid sequence of positions 53-68 of SEQ ID NO: 1 (and/or to an antibody that specifically binds to an epitope located within amino acids 53-68 of SEQ ID NO: 1; and/or to an antibody that specifically binds to a peptide the amino acid sequence of which comprises or consists of amino acids 53-68 of SEQ ID NO: 1).

The 356-amino acid sequence of SEQ ID NO: 1 corresponds to positions 20-375 of the known sequence of the human CD14 molecule according to e.g. Genbank accession no. AAH10507.1.

```
SEQ ID NO: 1:
Thr Thr Pro Glu Pro Cys Glu Leu Asp Asp Glu Asp
1               5                   10
Phe Arg Cys Val Cys Asn Phe Ser Glu Pro Gln Pro
            15                  20
Asp Trp Ser Glu Ala Phe Gln Cys Val Ser Ala Val
25                  30                  35
Glu Val Glu Ile His Ala Gly Gly Leu Asn Leu Glu
                40                  45
Pro Phe Leu Lys Arg Val Asp Ala Asp Ala Asp Pro
    50                  55                  60
Arg Gln Tyr Ala Asp Thr Val Lys Ala Leu Arg Val
            65                  70
Arg Arg Leu Thr Val Gly Ala Ala Gln Val Pro Ala
    75                  80
Gln Leu Leu Val Gly Ala Leu Arg Val Leu Ala Tyr
85                  90                  95
Ser Arg Leu Lys Glu Leu Thr Leu Glu Asp Leu Lys
            100                 105
Ile Thr Gly Thr Met Pro Pro Leu Pro Leu Glu Ala
    110                 115                 120
Thr Gly Leu Ala Leu Ser Ser Leu Arg Leu Arg Asn
                125                 130
Val Ser Trp Ala Thr Gly Arg Ser Trp Leu Ala Glu
        135                 140
Leu Gln Gln Trp Leu Lys Pro Gly Leu Lys Val Leu
145                 150                 155
Ser Ile Ala Gln Ala His Ser Pro Ala Phe Ser Cys
                160                 165
Glu Gln Val Arg Ala Phe Pro Ala Leu Thr Ser Leu
    170                 175                 180
Asp Leu Ser Asp Asn Pro Gly Leu Gly Glu Arg Gly
                185                 190
Leu Met Ala Ala Leu Cys Pro His Lys Phe Pro Ala
        195                 200
Ile Gln Asn Leu Ala Leu Arg Asn Thr Gly Met Glu
205                 210                 215
Thr Pro Thr Gly Val Cys Ala Ala Leu Ala Ala Ala
                220                 225
Gly Val Gln Pro His Ser Leu Asp Leu Ser His Asn
    230                 235                 240
Ser Leu Arg Ala Thr Val Asn Pro Ser Ala Pro Arg
                245                 250
```

```
                        -continued
Cys Met Trp Ser Ser Ala Leu Asn Ser Leu Asn Leu
        255                 260

Ser Phe Ala Gly Leu Glu Gln Val Pro Lys Gly Leu
265                 270                 275

Pro Ala Lys Leu Arg Val Leu Asp Leu Ser Cys Asn
            280                 285

Arg Leu Asn Arg Ala Pro Gln Pro Asp Glu Leu Pro
        290                 295                 300

Glu Val Asp Asn Leu Thr Leu Asp Gly Asn Pro Phe
                305                 310

Leu Val Pro Gly Thr Ala Leu Pro His Glu Gly Ser
            315                 320

Met Asn Ser Gly Val Val Pro Ala Cys Ala Arg Ser
325                 330                 335

Thr Leu Ser Val Gly Val Ser Gly Thr Leu Val Leu
            340                 345

Leu Gln Gly Ala Arg Gly Phe Ala
        350                 355     -
```

The term "sCD14-ST" as used herein refers to the peptide, which is also known as "soluble CD14 subtype" or "presepsin". sCD14-ST is derived from sCD14 (soluble CD14), of which at least two forms of higher molecular weight exist (49 kDa and 55 kDa) and of which sCD14-ST is a fragment. Proteolysis of sCD14 leads to generation of sCD14-ST. sCD14-ST, when electrophoresed under non-reducing conditions, has an apparent molecular weight of 13±2 kDa. Antibodies are available that specifically bind to sCD14-ST without binding to sCD14, thus allowing for discrimination between sCD14-ST and sCD14. On the other hand, an antibody can beneficially be excluded which may bind to sCD14, but does not recognize sCD14-ST.

The term "peptide or polypeptide" or "marker" as used herein means a compound selected from sCD14, sCD14-ST, or a fragment or derivative of sCD14 other than sCD14-ST or other suitable predictive marker described herein (though most preferably sCD14_ST), wherein according to a particular embodiment a combination of markers are determined, including but not limited to a neurohormonal marker, an ischemic cardiac marker, a marker of the transforming growth factor-β cytokine superfamily, interleukin receptor family, e.g. interleukin 1 receptor-like 1, also known as IL1RL1 and ST2, or neutrophil gelatinase-associated lipocalin (NGAL), and/or an inflammatory marker as respectively explained above. The term "peptide or polypeptide" or "marker" may additionally mean another peptide known in the art as risk marker.

It has been found that neurohormonal markers, markers, which are regulators of water balance, ischemic cardiac markers, markers of the transforming growth factor-β cytokine superfamily, interleukin receptor family, e.g. interleukin 1 receptor-like 1, also known as IL1RL1 and ST2, or neutrophil gelatinase-associated lipocalin (NGAL), and inflammatory markers represent groups of independent risk indicators. Thus, the combination of a compound selected from sCD14, sCD14-ST, or a fragment or derivative of sCD14 other than sCD14-ST as a novel cardiovascular marker with markers of said groups of markers as provided by the invention, results in a further increased sensitivity and specificity and, therefore, higher accuracy in the diagnosis of cardiovascular diseases or conditions or atherosclerosis or in evaluating a subject's risk of developing a cardiovascular disease or condition or atherosclerosis or in evaluating a subject's risk of mortality. It is further possible to identify with increased accuracy a subject that will benefit from a certain treatment. The increased accuracy also allows for discrimination between various cardiovascular diseases or conditions, such as discrimination between chronic heart failure and acute heart failure. In addition, the accuracy of the method according to the invention provides for a means to distinguish subjects in need of hospitalization from subjects that can be discharged. In a preferred embodiment of the invention the increased accuracy allows for identifying subjects having myocardial infarction (rule-in) and subjects that do not suffer from myocardial infarction (rule-out).

The method according to the invention according to this preferred embodiment comprises the determination of a compound selected from sCD14, sCD14-ST, or a fragment or derivative of sCD14 other than sCD14-ST, wherein the amount of said compound is determined as well as the amount of a neurohormonal marker, a regulator of water balance, an ischemic cardiac marker, a marker of the transforming growth factor-β cytokine superfamily, interleukin receptor family, e.g. interleukin 1 receptor-like 1, also known as IL1RL1 and ST2, or neutrophil gelatinase-associated lipocalin (NGAL), and/or one inflammatory marker in the same or in a different sample from the same subject.

The neurohormonal marker can be selected, for example, from atrial natriuretic peptide (ANP), brain (B-type) natriuretic peptide (BNP), or N-terminal fragments of the respective propeptides NT-proANP, proANP and NT-proBNP, NT-proBNP is preferred as a neurohormonal marker. The marker of water balance can be selected, for example, from peptides derived from pre-provasopressin, preferably copeptin. Copeptin is the C-terminal portion of pre-provasopressin.

cTn, for example, can be determined as an ischemic cardiac marker, preferably as a marker for myocardial infarction. In the multi-marker approach, the ischemic cardiac marker is preferably cTnT or cTnI and more preferably high-sensitivity cTnT (hsTnT) or high-sensitivity cTnI, and the reference amount of the ischemic cardiac marker is preferably about 8 pg/ml.

The inflammatory marker can be selected, for example, from C-reactive protein (CRP), interleukins, in particular IL-6, and adhesion molecules such as VCAM and ICAM. CRP or IL-6 are preferably determined as the inflammatory marker.

As to a use of an inflammatory marker according to a particular embodiment, an amount of C-reactive protein (CRP), in particular high-sensitivity C-reactive protein (hs-CRP) is determined in the same or different sample of the subject in addition to determining the amount of a compound selected from sCD14, sCD14-ST, or a fragment or derivative of sCD14 other than sCD14-ST, which preferred embodiment provides a greatly enhanced sensitivity of determination results and specificity of discriminating between subjects to be admitted to the hospital and eventually being subjected to intervention or subjects at risk of mortality, and subjects not considered further for clinical or medical treatments. C-reactive protein can be assayed by known methods (Roberts et al., Clin Chem 2001, 47: 418-425 [Erratum, Clin Chem 2001; 47:980.]), for example by rate nephelometry or by monoclonal-antibody, solid-phase, sandwich-type enzyme immunoassay (e.g. IMx, Abbott Laboratories, North Chicago), calibrated with the World Health Organization's International Reference Standard for CRP Immunoassay (85/506) (WHO Expert Committee on Biological Standardization. Thirty-seventh report. World Health Organ Tech Rep Ser 1987; 760:21-22.). The range of values detected by the assay typically is 0.05 to 30 pg/ml.

The median normal value for C-reactive protein typically is 0.8 pg/ml, with 90 percent of normal values <3 pg/ml and 99 percent <10.0 pg/ml. A reference amount, i.e. level for C-reactive protein of 4 pg/ml, and especially a level C-reactive protein of >10 pg/ml should preferably be the threshold for being admitted to the hospital.

In the multi-marker approach, the inflammatory marker is preferably procalcitonin (PCT) and the reference amount of PCT is preferably about 0.5 ng/ml, 2.0 ng/ml and 10 ng/ml.

The marker of the transforming growth factor-β cytokine superfamily can be selected, for example from TGF-β isoforms, preferably MIC-1 or GDF-15 can be determined; the reference amount of the marker of the transforming growth factor-β cytokine superfamily is preferably about 1.0 ng/ml.

As a marker of the interleukin receptor family, preferably IL1 RL1/ST2 may be selected.

The marker of water balance can be selected, for example, from pre-provasopressin-derived peptides, preferably copeptin. The reference amount of copeptin is preferably 11.25 pmol/L.

As a marker of kidney injury, preferably neutrophil gelatinase-associated lipocalin (NGAL) may be selected.

In certain embodiments, the amount of sCD14, sCD14-ST, or a fragment or derivative of sCD14 other than sCD14-ST, is determined in addition to that of at least one additional marker selected from a neurohormonal marker (e.g. NT-proBNP), an ischemic cardiac marker (e.g. hsTnT), an inflammatory marker (e.g. C-reactive protein, CRP) and a marker of the interleukin-1 receptor family (e.g. IL1RL1/ST2). In such embodiments, the disease or condition is a disease or condition within the meaning of the present invention, i.e. a cardiovascular disease or condition or atherosclerosis. It may be or include, e.g., acute heart failure. E.g., the disease or condition may also selected from the group consisting of acute coronary syndrome, acute heart failure, chronic heart failure, coronary artery disease, angina pectoris, myocardial infarction, ischemic stroke, hemorrhagic stroke, and/or transient ischemic attacks.

Preferably, the subject according to the invention presents to an emergency department, preferably in a hospital, even more preferably a medical emergency department.

In the context of the present invention, the term "emergency department" refers to any location where subjects feeling unwell or subjects looking for an evaluation of their individual risk of developing certain diseases present, in order to consult a person having a medical background, preferably a physician, to obtain an analysis of their physiological status and/or the cause underlying their discomfort. Typical examples are emergency departments or emergency rooms in hospitals, ambulances, medical doctors' practices or doctors' offices and other institutions suitable for diagnosis and/or treatment of subjects.

The method of the present invention is, preferably, an in vitro method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the determination in step (a) or a computer-implemented comparison in step (b).

The term "evaluating" as used herein means assessing whether a subject is at elevated risk for developing a cardiovascular condition or disease, whether a subject is in need of hospitalization or whether a subject will benefit from a specific treatment. As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention.

The term "predicting" used herein refers to assessing the probability according to which a subject will die within a defined time window (predictive window) in the future. The predictive window is an interval in which the subject will die according to the predicted probability. The predictive window may be the entire remaining lifespan of the subject upon analysis by the method of the present invention. Preferably, however, the predictive window is an interval of one month, six months or one, two, three, four, five or ten years after appearance of the cardiovascular complication (more preferably and precisely, after the sample to be analyzed by the method of the present invention has been obtained). As will be understood by those skilled in the art, such an assessment is usually not intended to be correct for 100% of the subjects to be analyzed. The term, however, requires that the assessment will be valid for a statistically significant portion of the subjects to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction will be correct for at least 60%, at least 70%, at least 80%, or at least 90% of the subjects of a given cohort.

The term "mortality" as used herein relates to mortality which is caused by cardiovascular complications, lung diseases, pulmonary embolism, thrombosis, thromboembolic complications, stroke, tumors and malignant diseases, sepsis, septic shock, bleeding disorders, organ failure, acute kidney disease, infectious diseases, gastrointestinal complications, pancreatits, rheumatic disorders and others.

The expression "evaluating the risk of mortality" as used herein means that it the subject to be analyzed by the method of the present invention is allocated either into the group of subjects of a population having a normal, i.e. non-elevated, risk for mortality or into a group of subjects having a significantly elevated risk. An elevated risk as referred to in accordance with the present invention means that the risk of mortality within a predetermined predictive window is elevated significantly for a subject with respect to the average risk for mortality in a population of subjects. Preferably, for a predictive window of one year, the average risk is within the range of 0.5 and 3.0%, preferably, 1.5%.

An elevated risk as used herein, preferably, relates to a risk of more than 3.0%, preferably, more than 5.0%, and, most preferably within 3.0% and 8.0% with respect to a predictive window of one year. The time horizon over which such risk stratification may be applied (that is, the period for which prognostic risk may be predicted) may be from 1 day to 5 years, more preferably from 1 week to 2 years, and from 1 month to 1 year.

In general, the amount of a compound selected from sCD14, sCD14-ST, or a fragment or derivative of sCD14 other than sCD14-ST or the at least one additional marker is determined in a healthy reference population and in subjects suffering from a cardiovascular disease or condition or atherosclerosis in order to determine a reference value for the respective markers and threshold values, respectively, that are associated with a certain physiological status. The results of the measurements are analyzed by statistical methods known to the skilled person, such as ROC (receiver operating characteristic) analysis. A threshold value is determined for a specific cardiovascular disease or condition or atherosclerosis or for a certain risk status of the subject, wherein the threshold is selected in such a manner as to obtain an assay specificity and/or sensitivity, which is suitable for the specific use. In a preferred embodiment, the threshold values are chosen in view of the distribution of the values in a population. It may be useful, for example, to choose the median value, the $60^{th}$, the $70^{th}$, the $80^{th}$, the $90^{th}$, the $95^{th}$, the 9e or the $99^{th}$ percentile of the healthy and/or non-healthy group in order to establish the reference value and the threshold value, respectively.

The amount of a compound selected from sCD14, sCD14-ST, or a fragment or derivative of sCD14 other than sCD14-ST determined in a sample of a subject is then compared to the amount of said compound in a healthy reference population. A diagnosis/an evaluation is made on the basis of thresholds that have been set for a given physiological status.

The combined determination according to the invention is preferably performed so that parallel determinations of the markers are performed in one or more samples from a patient to be investigated. Preferably, one or more samples collected from the patient, e.g., whole blood samples, or plasma samples, or serum samples, are investigated in one or more tests simultaneously or immediately sequentially. The determinations are performed particularly preferably in a single patient sample.

The combined determination of markers can be performed, in principle, based on any known method using common commercial assays. Automated analyzers can be used for the determination, for example. As an alternative, rapid assays, or assays of Point of Care (POC) analysis systems for use in the emergency room, in the hospital ward or intensive care station, in the ambulance or doctor's office, or as a patient self-test can also be used.

Determining the amount of a compound selected from sCD14, sCD14-ST, or a fragment or derivative of sCD14 other than sCD14-ST or of any other peptide or polypeptide (marker as used herein) referred to in this specification relates to measuring the amount or concentration, preferably semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

Preferably, measurement of the amount of a compound selected from sCD14, sCD14-ST, or a fragment or derivative of sCD14 other than sCD14-ST is performed using an antibody such as a polyclonal antibody and preferably a monoclonal antibody, which is specific for said compound. In a preferred embodiment, the antibody specifically binds sCD14-ST without binding to sCD14 or CD14. Such specificity is obtained, for example, if an antibody is raised against the region between b3 and b4 in the CD14 secondary structure (i.e. amino acid 36 to 79 in human CD14).

In accordance with the present invention, determining the amount of a peptide or polypeptide (marker as used herein) can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (AccuTnI, Beckmann-Coulter Diagnostics; Architect cTnI and AxSYM cTnI, Abbott Diagnostics; ADVIA Centaur XP cTNI, Bayer Healthcare; Immulite 2500 cTnI, Diagnostics Product Corporation; Elecsys cTnT, Roche Diagnostics), CBA (an enzymatic Cobalt Binding Assay, available for example on Roche-Hitachi analyzers), LIAISON® BRAHMS PCT®, KRYPTOR Random Access Analyser, BRAHMS PCT LIA, BRAHMS PCT-Q and latex agglutination assays (available for example on Roche-Hitachi$^M$ analyzers, PATHFAST chemiluminescent enzyme immunoassay system (CLEIA), Mitsubishi Chemical Medience Corporation, Tokyo, Japan).

Preferably, determining the amount of a peptide or polypeptide (marker as used herein) comprises the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide.

Also preferably, determining the amount of a peptide or polypeptide (marker as used herein) comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide (marker as used herein) may, preferably, comprises the steps of (a) contacting the peptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)$_2$ fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels (e.g. "magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), chemiluminescent substrate (CDP-STAR, Amersham Biosciences), fluorescence detection substrate (ECF, Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}$S, $^{125}$I, $^{32}$P, $^{33}$P and the like. A radioactive label can be detected by any method known and appropriate, e.g. a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

The amount of a peptide or polypeptide (marker as used herein) may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide (marker as used herein), the relative amount or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the peptide or polypeptide (marker as used herein) comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amount determined in step a) and the reference amount, it is possible to assess whether a subject is susceptible for a cardiac intervention, i.e. belonging to the group of subjects which can be successfully treated by the cardiac intervention. Therefore, the reference amount is to be chosen so that either a difference or a similarity in the compared amounts allows identifying those the test subject which belong into the group of subjects susceptible for cardiac intervention or identifying those test subjects which are not susceptible for a cardiac intervention.

Accordingly, the term "reference amount" as used herein refers to an amount of the respective marker as used herein which allows assessing whether a subject is to be admitted to the hospital or to an intensive care unit, or can be discharged to home. Accordingly, the reference may e.g. be derived from (i) a subject known to have been successfully admitted to the hospital, i.e. who has been subject to further examination and subsequent treatment or intensive care treatment based on the results of the further investigation without the occurrence of adverse effects such as mortality or side effects caused by non-adapted treatment regimen, or (ii) a subject known to have not been admitted to the hospital and which died or developed side effects caused by non-adapted treatment regimen. Moreover, the reference amount may define a threshold amount, whereby an amount larger than the threshold shall be indicative for a subject which should be admitted to the hospital for further examination and/or intensive treatment, while an amount lower than the threshold amount shall be an indicator for a subject which can not be discharged to home. The reference amount applicable for an individual subject may vary depending on various physiological parameters such as age, gender, or subpopulation, as well as on the means used for the determination of the polypeptide or peptide referred to herein (marker as used herein). A suitable reference amount may be determined by the method of the present invention from a reference sample to be analyzed together, i.e. simultaneously or subsequently, with the test sample. A preferred reference amount serving as a threshold may be derived from the upper reference limit (URL) of normal, i.e. the upper limit of the physiological amount to be found in a population of apparently healthy subjects. The URL for a given population of subjects can be determined by various well known techniques. A suitable technique may be to determine the median of the population for the peptide or polypeptide amounts to be determined in the method of the present invention. A preferred threshold (i.e. reference amount) for a compound selected from sCD14, sCD14-ST, or a fragment or derivative of sCD14 other than sCD14-ST is at least one to two times the lower detection limit. For example, the lower detection limit of the PATHFAST sCD14-ST assay referred to in this context is, preferably, 20 pg/ml.

Thus, in a preferred embodiment of the invention, the reference amount defining a threshold amount for a compound selected from sCD14, sCD14-ST, or a fragment or derivative of sCD14 other than sCD14-ST—preferably sCD14-ST—is 20 pg/ml and below the $99^{th}$ percentile, below the $97.5^{th}$ or below the $95^{th}$ or below the $90^{th}$ percentile of an apparently healthy population.

An amount of a compound selected from sCD14, sCD14-ST, or a fragment or derivative of sCD14 other than sCD14-ST larger than the reference amount is, more preferably, indicative for a subject having a cardiovascular disease or condition or atherosclerosis or for a subject at an elevated risk of developing a cardiovascular disease or condition or atherosclerosis. In a further preferred embodiment, an amount of the compound higher than the reference amount is characteristic for a subject, whose physiological status requires the initiation of suitable therapeutic measures and/or admission to a hospital. An amount of the compound higher than the reference amount preferably indicates a subject, which will benefit from a treatment with a substance selected from the group consisting of antibiotics, probiotics and lactulose. In another preferred embodiment, an amount of the compound higher than the reference amount is indicative for subjects at an increased risk of mortality.

Advantageously, it has been found in the study underlying the present invention that a compound selected from sCD14, sCD14-ST, or a fragment or derivative of sCD14 other than sCD14-ST is a reliable prognostic biomarker for assessing the success of cardiac interventions for subjects in need thereof, i.e. subjects which suffer from cardiovascular diseases or conditions or atherosclerosis and, in particular, those which are affected by acute cardiovascular events or heart failure, for example acute heart failure. Thanks to the present invention, a risk/success stratification can be easily performed before subjecting a patient to a cardiac intervention. In case the patient turns out to be not susceptible for a cardiac intervention, said dangerous, time and/or cost intensive therapy can be avoided. Thus, besides preventing a subject from the adverse and severe side effects accompanying a cardiac intervention, the method of the present invention will be beneficial for the health system in that resources will be saved. It is to be understood that according to the method of the present invention described herein above and below, the amount of a compound selected from sCD14, sCD14-ST, or a fragment or derivative of sCD14 other than sCD14-ST or means for the determination thereof can be used for the manufacture of a diagnostic composition for identifying a subject being susceptible for a cardiac intervention.

In a preferred embodiment, the method according to the invention is used for risk assessment in a subject having multiple organ dysfunction syndrome (MODS).

In addition or alternatively, the above method of the present invention may be used to identify a subject susceptible to intensive care treatment in an intensive care unit. The intensive care treatment may comprise additional diagnostic procedures, e.g. transthoratic echocardiography (TTE), transesophageal echocardiography (TEE), abdominal ultrasound examination, CT-scan of the chest, chest radiography, high-resolution CT-scan, cardiac catheterisation (left 6 right heart), perfusion/inhalation scintigraphy, compression ultrasound examination, treadmill exercise ECG, bronchoscopy, phlebography, angiography, and CT arteriogram (CTA) or magnetic resonance arteriogram (MRA) of the brain. In case of cardiac diseases, thromboembolic complications, stroke or pulmonary embolism, cancer and other extracardiac diseases a therapy comprises PCI, different surgical procedures, e.g. embolectomy, and specific medication e.g. oxygen, oral anticoagulation with vitamin K antagonists, anticoagulation with unfractionated heparins, LMW heparins, other antithrombotica, thrombolytic drugs, acetylsalicyclic acid, clopidigrel, loops diuretics and other diuretics, beta-blockers, ACE inhibitors, digitalis, calcium antagonists, nitrates, steroids, theophyllin, beta-2 mimetics, other bronchodilators, NSAIDs, opiates, antibiotics etc. Therapeutic intervention comprises all kinds of surgery and medications.

Preferably, the said therapy to be selected for a subject by the method of the present invention said therapy is a drug-based therapy. More preferably, the said medicament is an ACE inhibitor, preferably captopril, enalapril, fosinopril, lisinopril, perindopril, quinapril, ramipril, or trandolapril, an AT-1 receptor blocking agent, preferably, candesartan, losartan, or valsartan, a β-receptor blocking agent, preferably, bisoprolol, carvedilol, metoprolol or succinate, or an an aldosterone antagonist, preferably, spironolacton or eplerenone, preferably, treatment with lactulose, probiotics and antibiotics.

In a preferred embodiment of the invention, antibiotics are used for treatment, which are not resorbed by the gut. In a further preferred embodiment, aminoglycoside antibiotics are employed. Preferably, neomycin and paromycin is used.

Another preferred therapy to be selected for a subject in accordance with the present invention is an interventional therapy. An interventional therapy as referred to herein is a therapy which is based on physical interventions with the subject, e.g., by PCI, surgery, and/or electrophysiological interventions. More preferably, said interventional therapy is cardiac resynchronisation therapy (CRT) or based on implantation of a cardioverter defibrillator (ICD).

Encompassed by the present invention is, further, a device for identifying a subject to be admitted to the hospital, adapted to carry out the method of the present invention, comprising means for determining the amount of a compound selected from sCD14, sCD14-ST, or a fragment or derivative of sCD14 other than sCD14-ST in a sample of the subject and means for comparing said amount to a reference amount, whereby a subject at elevated risk necessitating to initiation of suitable therapeutic measures or indicative for a subject which should be admitted to the hospital is identified.

The term "device" as used herein relates to a system of means comprising at least the aforementioned means operatively linked to each other as to allow the prediction. Preferred means for determining the amount of a compound selected from sCD14, sCD14-ST, or a fragment or derivative of sCD14 other than sCD14-ST and means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g. a computer program in order to obtain the desired results. Preferably, the means are comprised by a single device in such a case. Said device may accordingly include an analyzing unit for the measurement of the amount of the peptides or polypeptides in an applied sample and a computer unit for processing the resulting data for the evaluation. Alternatively, where means such as test stripes are used for determining the amount of the peptides or polypeptides, the means for comparison may comprise control stripes or tables allocating the determined amount to a reference amount. The test stripes are, preferably, coupled to a ligand which specifically binds to the peptides or polypeptides referred to herein. The strip or device, preferably, comprises means for detection of the binding of said peptides or polypeptides to the said ligand. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test stripes or electronic devices which merely require loading with a sample. The results may be given as output of raw data which need interpretation by the clinician. Preferably, the output of the device is, however, processed, i.e. evaluated, raw data the interpretation of which does not require a clinician. Further preferred devices comprise the analyzing units/devices (e.g., biosensors, arrays, solid supports coupled to ligands specifically recognizing the natriuretic peptide, Plasmon surface resonance devices, NMR spectrometers, mass-spectrometers etc.) or evaluation units/devices referred to above in accordance with the method of the invention.

Moreover, the present invention also relates to a device for predicting the risk of mortality or a further acute cardiovascular event for a subject adapted to carry out the method of the present invention comprising means for determining the amounts of the peptide or polypeptide (marker as used herein) in a same or different sample of a subject and means for comparing said amounts to reference amounts, whereby it is predicted whether a subject is at risk of mortality or a acute cardiovascular event.

Further envisaged is a device for deciding about admitting a subject to the hospital, adapted to carry out the method of the present invention, comprising means for determining the amount of a compound selected from sCD14, sCD14-ST, or a fragment or derivative of sCD14 other than sCD14-ST or a variant thereof in a sample of the said subject and means for comparing said amount to a reference amount, whereby it is decided whether the subject is to be admitted to the hospital.

The present invention also relates to a device for evaluating elevated risk for developing a cardiovascular disease or condition or atherosclerosis requiring the initiation of suitable therapeutic measures comprising means for determining the amount of a compound selected from sCD14, sCD14-ST, or a fragment or derivative of sCD14 other than sCD14-ST in a sample of the subject and means for comparing said amounts to reference amounts, whereby it is predicted whether the subject is at risk for developing a cardiovascular disease or condition or atherosclerosis.

The present invention also relates to a device for evaluating the risk of mortality in a subject, adapted to carry out the method of the present invention, comprising means for determining the amount of a compound selected from sCD14, sCD14-ST, or a fragment or derivative of sCD14 other than sCD14-ST in a sample of the subject and means for comparing said amounts to reference amounts, whereby it is predicted whether the subject is at risk of mortality.

Furthermore, a kit for carrying out the methods of the present invention, for identifying a subject at elevated risk for developing a cardiovascular disease or condition or atherosclerosis or to be admitted to the hospital, deciding about admitting a subject to the hospital, or predicting the risk of mortality in a subject is envisaged by the present invention. Said kit comprising means for determining the amount of a compound selected from sCD14, sCD14-ST, or a fragment or derivative of sCD14 other than sCD14-ST or a variant thereof in a sample of a subject and means for comparing said amounts to reference amounts, wherein a subject at elevated risk for developing a cardiovascular disease or condition or atherosclerosis or to be admitted to the hospital is identified, a decision about initiation of suitable therapeutic measures or about admitting the subject to the hospital or to an intensive care unit is made, or the risk of mortality in the subject is predicted.

The term "kit" as used herein refers to a collection of the aforementioned means, preferably, provided in separately or within a single container. The container, also preferably, comprises instructions for carrying out the method of the present invention.

It is to be understood that the definitions and explanations of the terms made above and below apply accordingly for all embodiments described in this specification and the accompanying claims.

1. Evaluation of a Subject's Risk of Developing a Cardiovascular Disease

Determining a compound selected from sCD14, sCD14-ST, or a fragment or derivative of sCD14 other than sCD14-ST and comparing it with a respective reference amount provides a high predictive value for identifying if a subject is at elevated risk for developing a cardiovascular disease or condition or atherosclerosis that requires suitable therapeutic measures. In particular, the method allows for determining the risk of developing a cardiovascular disease or condition or atherosclerosis also in a subject, which is free from any clinical signs or symptoms indicating such disease or condition or atherosclerosis.

Preferably, the subject having an elevated risk of developing a cardiovascular disease or condition or atherosclerosis is characterized in that an amount of a compound selected from sCD14, sCD14-ST, or a fragment or derivative of sCD14 other than sCD14-ST—most preferably sCD14-ST—determined in a sample from said subject that is preferably 225 pg/ml or higher, more preferably 240 pg/ml or higher, even more preferably 260 pg/ml or higher.

Typically, a comparison with a healthy reference population is applied in order to identify thresholds with respect to elevated levels of a compound selected from sCD14, sCD14-ST, or a fragment or derivative of sCD14 other than sCD14-ST. The reference amount of such a compound (most preferably sCD14-ST) in healthy subjects is preferably between 223 pg/ml and 262 pg/ml.

2. Diagnosis of a Cardiovascular Disease or Condition or Atherosclerosis in a Subject According to a preferred embodiment of the invention, a method is provided for diagnosing a cardiovascular disease or condition or atherosclerosis in a subject. Preferably, a diagnosis is provided for one or more cardiovascular diseases or conditions selected from the group consisting of acute coronary syndrome, acute heart failure, chronic heart failure, coronary artery disease, angina pectoris, myocardial infarction, ischemic stroke, hemorrhagic stroke and transient ischemic attacks.

The method is further useful for assessing a prognosis of a subject with a cardiovascular disease or condition or atherosclerosis.

In a preferred embodiment, the method is used for discriminating between various cardiovascular diseases or conditions or atherosclerosis.

a) Diagnosis of Chronic Heart Failure

According to the invention, a method is for provided for diagnosing chronic heart failure, preferably wherein the amount of a compound selected from sCD14, sCD14-ST, or a fragment or derivative of sCD14 other than sCD14-ST—most preferably sCD14-ST—is 115 pg/ml or higher, more preferably 150 pg/ml or higher, even more preferably 260 pg/ml or higher. In an alternative embodiment, the amount of the compound (preferably sCD14-ST) is between 115 pg/ml and 4000 pg/ml, more preferably between 150 pg/ml and 3000 pg/ml, even more preferably between 260 pg/ml and 2000 pg/ml.

b) Diagnosis of Angina Pectoris

As a further embodiment of the invention, a method is provided for diagnosing angina pectoris, preferably wherein the amount of a compound selected from sCD14, sCD14-ST, or a fragment or derivative of sCD14 other than sCD14-ST—most preferably sCD14-ST—is 214 pg/ml or higher, more preferably 216 pg/ml or higher, even more preferably 222 pg/ml or higher. Alternatively, the amount of the compound (preferably sCD14-ST) in a subject having angina pectoris is between 214 pg/ml and 4000 pg/ml, more preferably between 216 pg/ml and 3000 pg/ml, even more preferably between 222 pg/ml and 2000 pg/ml.

c) Diagnosis of Acute Heart Failure

Acute heart failure can be diagnosed by the method according to the invention. Therein, the amount of a compound selected from sCD14, sCD14-ST, or a fragment or derivative of sCD14 other than sCD14-ST—most preferably sCD14-ST—in a subject having acute heart failure is 295 pg/ml or higher, more preferably 354 pg/ml or higher, even more preferably 455 pg/ml or higher. Alternatively, the amount of the compound (preferably sCD14-ST) is between 295 pg/ml and 4000 pg/ml, more preferably between 354 pg/ml and 3000 pg/ml, even more preferably between 455 pg/ml and 2000 pg/ml.

In a further preferred embodiment, the method is applied for diagnosing acute decompensated heart failure (ADHF) in a subject.

Moreover, the method according to the invention allows for discriminating between chronic heart failure and acute heart failure. Therein, the amount of a compound selected from sCD14, sCD14-ST, or a fragment or derivative of sCD14 other than sCD14-ST—most preferably sCD14-ST—in a sample from a subject having acute heart failure is preferably 340 pg/ml or higher, more preferably 354 pg/ml or higher, even more preferably 455 pg/ml or higher.

d) Diagnosis of Myocardial Infarction

In a preferred embodiment of the invention, the method is for diagnosing myocardial infarction. It has been found that myocardial infarction is characterized by the presence of an amount of a compound selected from sCD14, sCD14-ST, or a fragment or derivative of sCD14 other than sCD14-ST—most preferably sCD14-ST—in a sample from a subject, which is preferably 260 pg/ml or higher, more preferably 276 pg/ml or higher, even more preferably 295 pg/ml or higher.

Alternatively, the amount of the compound (preferably sCD14-ST) indicative of myocardial infarction is between 260 pg/ml and 4000 pg/ml, more preferably between 276 pg/ml and 3000 pg/ml, even more preferably between 295 pg/ml and 2000 pg/ml.

Using the method according to the invention, rule-out of myocardial infarction using a compound selected from sCD14, sCD14-ST, or a fragment or derivative of sCD14 other than sCD14-ST could be already possible at admission to the emergency department. Advantageously, according to the invention a diagnosis based on said compound can be provided immediately and a single sample is sufficient. This is a particular advantage with respect to conventional cTn measurements, which are dependent on the detection of a rise and/or fall in cTn, thus requiring at least two cTn measurements. Furthermore, the diagnostic and prognostic power of a compound selected from sCD14, sCD14-ST, or a fragment or derivative of sCD14 other than sCD14-ST is superior as compared to prior art markers such as cTn.

Alternatively, cTn levels can be determined in combination with the amount of sCD4-ST in order to even further increase accuracy.

3. Evaluation of a Subject's Risk of Mortality

According to the invention, a method is provided for identifying a subject having a cardiovascular disease or condition or atherosclerosis that has an elevated risk of mortality. Therein, the amount of a compound selected from sCD14, sCD14-ST, or a fragment or derivative of sCD14 other than sCD14-ST—most preferably sCD14-ST—is preferably 500 pg/ml or higher, more preferably 800 pg/ml or higher, even more preferably 1300 pg/ml. Alternatively, the amount of the compound (preferably sCD14-ST) in a subject having an elevated risk of mortality is between 500 pg/ml and 4000 pg/ml, more preferably between 800 pg/ml and 3000 pg/ml, even more preferably between 1300 pg/ml and 2000 pg/ml.

In particular, the risk of mortality in patients with acute heart failure can be assessed by use of the determination of a compound selected from sCD14, sCD14-ST, or a fragment or derivative of sCD14 other than sCD14-ST. Patients with heart failure, especially with acute heart failure, in general exhibit a high mortality. The concentration of a compound selected from sCD14, sCD14-ST, or a fragment or derivative of sCD14 other than sCD14-ST can identify heart failure patients with an elevated risk of mortality. Patients with elevated risk of mortality as assessed by sCD14-ST concentration had in general more advanced heart failure than those who survived.

4. Evaluation of Whether a Subject with a Cardiovascular Disease or Condition or Atherosclerosis will Benefit from a Specific Treatment Active carrier-mediated intestinal transport is reduced in acute chronic heart failure indicating epithelial dysfunction as a consequence of intestinal ischemia and higher lipopolysaccharid (LPS) concentrations in edematous heart failure which relates to inflammation. This finding is consistent with the observation of hypoxic and/or edematous intestine, which results in disruption of the epithelial barrier function and penetration of bacteria, as has also been found in spontaneous bacterial peritonitis in patients with liver cirrhosis and portal hypertension.

It has been found that elevated levels of a compound selected from sCD14, sCD14-ST, or a fragment or derivative of sCD14 other than sCD14-ST are indicative of subjects, in particular subjects with heart failure, will benefit from the use of antibiotics. Thus, the method according to the invention is for evaluating whether a subject will benefit from the treatment with substance selected from the group consisting of antibiotics, probiotics and lactulose. Preferably, antibiotics are employed that are not absorbed by the gut such as neomycin or paromycin. Generally, aminoglycoside antibiotics are preferred. Also additional treatments with lactulose and probiotics, which can change the flora of the gut, are particularly beneficial when applied to those subjects.

Based on this finding, the invention provides new therapeutic concepts, in that a substance selected from the group consisting of antibiotics, probiotics and lactulose is provided for use in the treatment of a subject having an increased plasma level of a compound selected from sCD14, sCD14-ST, or a fragment or derivative of sCD14 other than sCD14-ST. Preferably, the plasma level of the compound (preferably sCD14-ST) therein is 345 pg/ml or higher, preferably 800 pg/ml or higher, more preferably 1300 pg/ml or higher.

According to the present invention, a substance is provided for use in a treatment, which is not a treatment of sepsis or a disease associated with phagocyte dysfunction such as uremia, decrease in the activity of serum opsonin, complement deficiency, congenital phagocytosis dysfunction, chronic granulomatous disease, myeloperoxidase defect, leukemia, malignant lymphoma, bacterial endocarditis, diabetes and hepatic cirrhosis.

5. Determining Whether an Individual Subject Needs to be Hospitalized

Preferably, the method according to the present invention permits identifying if a subject is to be admitted to the hospital or an intensive care unit ("rule-in") or can be discharged ("rule-out"). In most cases, the subject presents to the emergency department. The method is based on the determination of a compound selected from sCD14, sCD14-ST, or a fragment or derivative of sCD14 other than sCD14-ST in a sample of the said subject. Thus a method is provided for determining whether a subject needs to be hospitalized due to a cardiovascular disease or condition or atherosclerosis.

Hospitalization of a subject is generally required if the amount of the compound (preferably sCD14-ST) is between 260 pg/ml and 4000 pg/ml, more preferably between 276 pg/ml and 3000 pg/ml, more preferably between 295 pg/ml and 2000 pg/ml, more preferably between 340 pg/ml and 4000 pg/ml, more preferably between 354 pg/ml and 3000 pg/ml, even more preferably between 455 pg/ml and 2000 pg/ml.

EXAMPLE 1

We herewith demonstrate that use of sCD14-ST improves detection of subjects at elevated risk for developing a cardiovascular disease or condition, diagnosis of acute coronary syndrome (ACS), acute myocardial infarction (MI), and acute heart failure (AHF) as well as decision making in the emergency room and the overall management of patients presenting to emergency departments by evaluating the diagnostic and prognostic power of sCD14-ST and prospectively examining the clinical impact of sCD14-ST concentration guided decision making regarding discharge, admission to hospital, intensive care treatment, prevention, and therapeutic measures in cardiovascular diseases or conditions. sCD14-ST was measured in samples obtained from a control group of healthy individuals and patients with different cardiac diseases:

Chronic heart failure (HF), n=40
Angina pectoris (AP) and unstable angina pectoris (UAP), n=17
Non-ST-elevation myocardial infarction (NSTEMI), n=29
Acute decompensated heart failure (ADHF), n=60
Control group, n=119

The measured sCD14-ST levels differed in a highly significant manner between healthy controls and patients with cardiovascular diseases as well as between the different patient groups (FIG. 1).

sCD14-ST was determined using the PATHFAST Presepsin assay (Mitsubishi Chemical Medience)

EXAMPLE 2

Reference Interval

A healthy control group (reference population) was used including 60 men and 59 women (age ranging from 21 to 69 years, median age 42 years) who fulfilled the following criteria: chronic diseases and intake of medications were excluded by questionnaire; physical examination, assessment of blood pressure, ECG registrations, and oral glucose tolerance tests yielded no pathological findings; plasma concentrations of N-terminal pro-B-type natriuretic peptide were 125 pg/ml; concentrations of TSH, creatinine and HbA1c were normal; cardiovascular diseases were excluded by cardiac magnetic resonance imaging including a dobutamine stress test.

sCD14-ST concentrations were determined in EDTA plasma samples of the control group using the PATHFAST assay. The 99th percentile upper reference limit (URL) according to the Clinical Laboratory Standard Institute (CLSI) Guideline C28-A3 was 258 (90% CI: 237-276) pg/ml. The results are displayed in Tab. 1.

TABLE 1

| sCD14-ST concentration of the healthy reference population (N = 119): | |
|---|---|
| Mean | 151 (95% CI: 141-159) pg/ml |
| Median | 143 (95% CI: 133-150) |
| Min | 60 pg/ml |
| Max | 311 pg/ml |
| IQR | 115-174 pg/ml |
| 99% Upper Reference Limit (URL)* | 258 (90% CI: 237-276) pg/ml |

*)Robust method CLSI C28-A3

EXAMPLE 3 sCD14-ST Levels in Patients with Chronic Heart Failure (CHF)

sCD14-ST concentrations were measured in EDTA plasma samples obtained from 40 patients with chronic heart failure (New York Health Association (NYHA) classification I-III).

TABLE 2

| sCD14-ST concentrations (pg/ml) in patients with CHF in comparison to the control group | | |
|---|---|---|
| | Control group | CHF, NYHY I-III |
| Sample size | 119 | 40 |
| Lowest value | 60 | 83 |
| Highest value | 311 | 533 |
| Median | 143 | 168 |
| 95% CI for the median | 133 to 150 | 156 to 191 |
| Interquartile range | 115 to 174 | 144 to 259 |
| Mann-Whitney test (independent samples) | | |
| Average rank of first group | | 68.9554 |
| Average rank of second group | | 97.625 |
| Mann-Whitney U | | 1395 |
| Test statistic Z (corrected for ties) | | 3.536 |
| Two-tailed probability | | P = 0.0004 |

Figure 2:
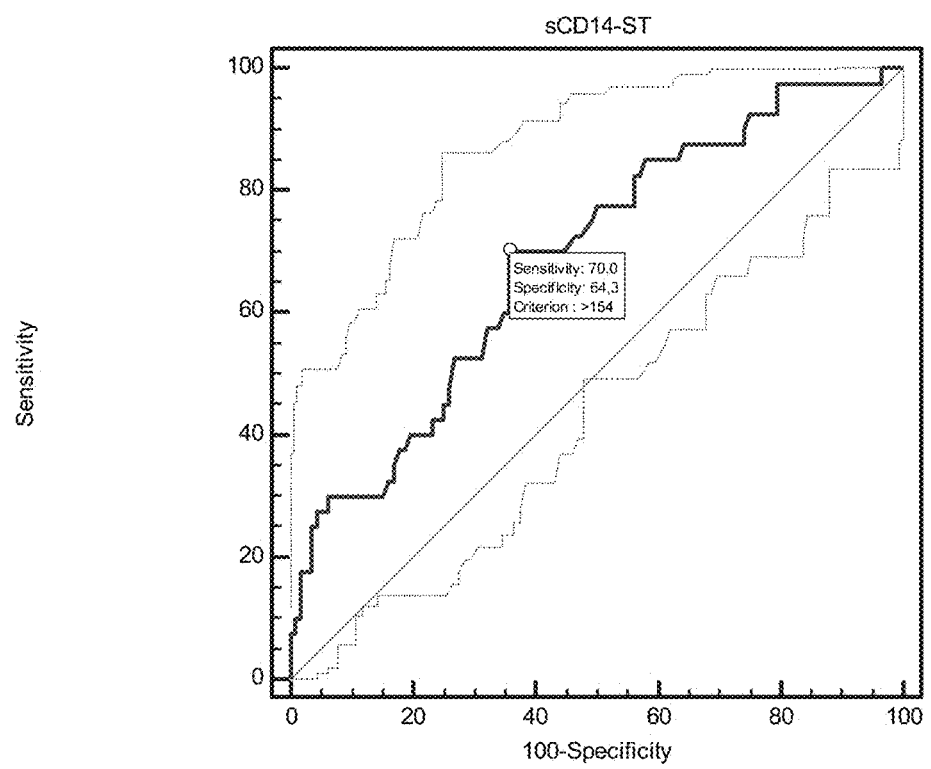
FIG. 2: ROC analysis for discrimination between the healthy control group and subject with CHF.

The sCD14-ST values were significantly (p=0.0004) elevated in CHF patients compared to the control group (Tab. 2). The ROC analysis (see Tab. 3) revealed an AUC of 0.689 (Sensitivity=70%, NPV=86%; Specificity=64%, PPV=41.2%) showing the discriminatory power of sCD14-ST between healthy controls and patients with CHF (see FIG. 2). This effect might be due to the underlying inflammatory process involved in the pathogenesis of cardiac diseases.

TABLE 3

| Results of ROC analysis for discrimination between controls and patients with CHF | |
|---|---|
| Variable | sCD14_ST |
| Classification variable | CHF |
| Sample size | 152 |
| Positive group: CHF = 1 | 40 |
| Negative group: CHF = 0 | 119 |
| Disease prevalence (%) | 26.3 |
| Area under the ROC curve (AUC) | 0.689 |
| Standard Error[a] | 0.0484 |
| 95% Confidence interval[b] | 0.609 to 0.761 |
| z statistic | 3.894 |

TABLE 3-continued

Results of ROC analysis for discrimination between controls and patients with CHF

| | |
|---|---|
| Significance level P (Area = 0.5) | 0.0001 |
| Youden index J | 0.3429 |
| Associated criterion | >154 |

EXAMPLE 4 sCD14-ST Levels in Patients with Unstable Angina Pectoris (UAP)

Figure 3:
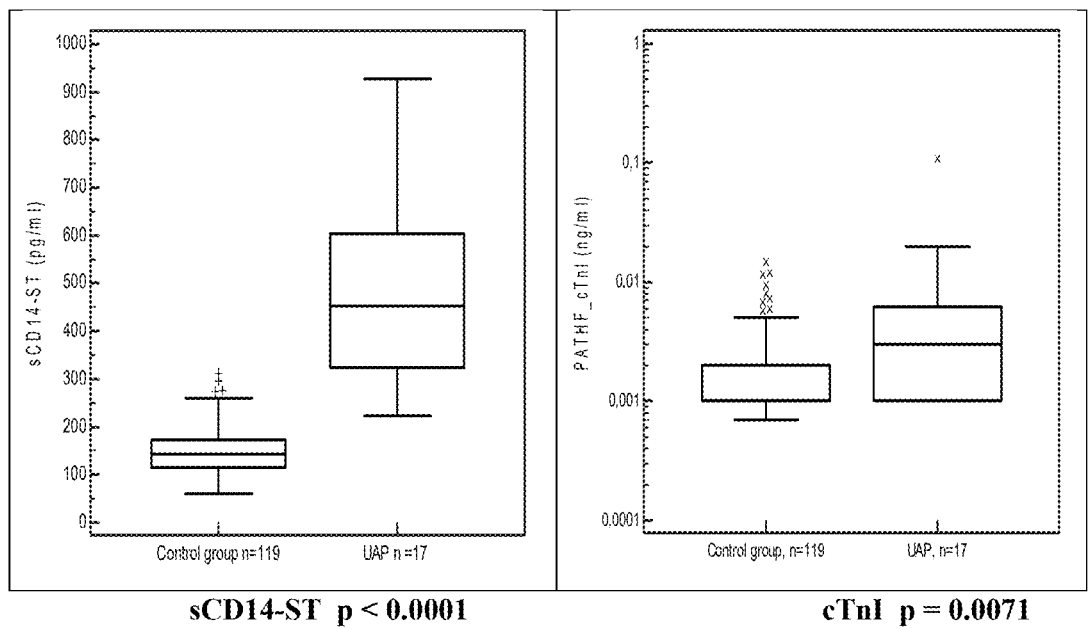
FIG. 3: sCD14-ST plasma concentrations of the healthy control group and subjects with unstable angina pectoris (UAP) at admission to the emergency room in comparison with the concentrations of cardiac troponin I (cTnI)

The sCD14-ST values were measured in patients presenting with unstable angina pectoris at the emergency room (Tab. 4). The difference to the corresponding values of the healthy control group revealed a high significance (p<0.0001), which was superior to cardiac troponin I (cTnI; see FIG. 3).

TABLE 4 sCD14-ST in patients with unstable angina pectoris (UAP, n = 17):

| | |
|---|---|
| Mean | 475 (95% CI: 380-570) pg/ml |
| Median | 452 (95% CI: 333-602) |
| Min | 223 pg/ml |
| Max | 928 pg/ml |
| 25$^{th}$ percentile | 324 (95% CI: 250-447) pg/ml |
| 75$^{th}$ percentile | 604 (95% CI: 460-780) pg/ml |

Figure 4:
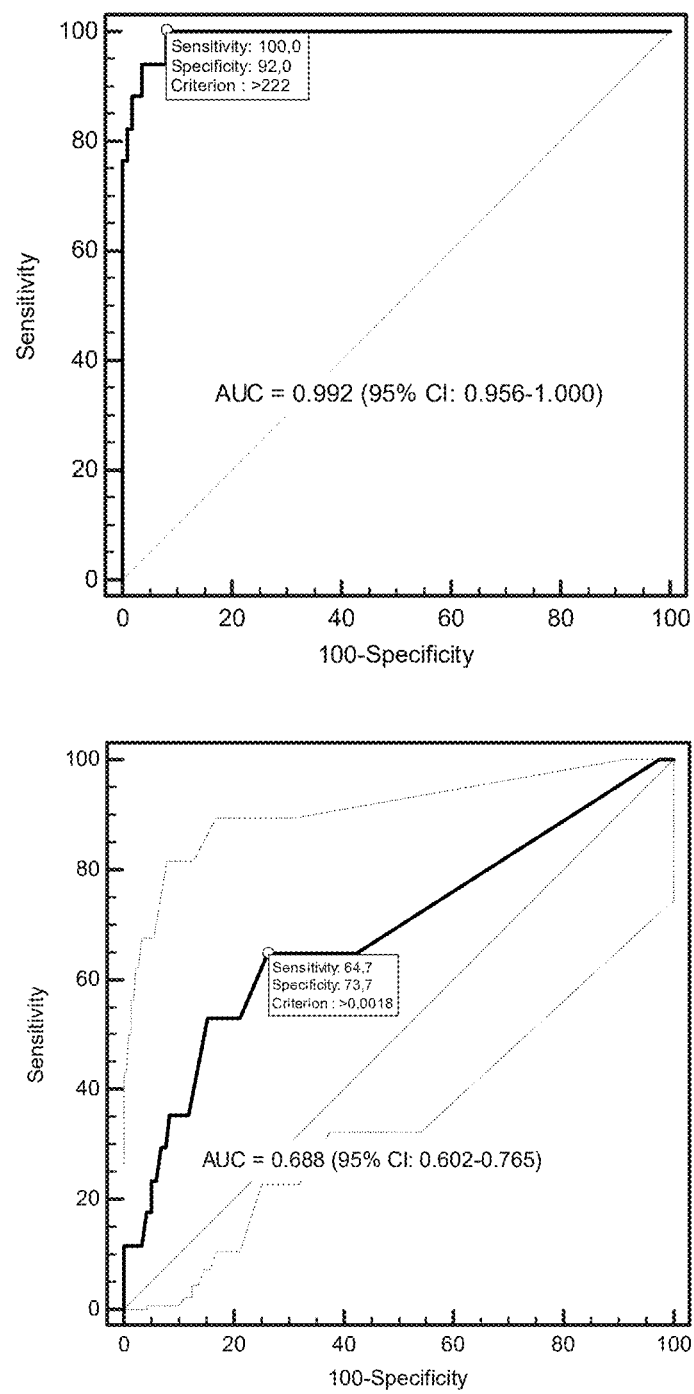
FIG. 4: Comparison of ROC curves of sCD14-ST (top panel) and cardiac troponin I (cTnI; bottom panel) for discrimination of subjects with unstable angina pectoris (UAP) and the healthy control group.

In parallel, the cTnI concentrations were measured using the PATHFAST cTnI assay. Surprisingly, sCD14-ST showed a higher discriminatory power between the healthy control group and UAP patients compared to cTnI. This finding could be confirmed by ROC analysis (FIG. 4) revealing a significantly higher AUC for sCD14-ST (0.996 vs 0.681, p=0.0001).

The results explain the finding that elevated sCD14-ST concentrations reflect the inflammatory process in the pathogenesis of atherosclerotic and cardiovascular diseases, which could be demonstrated by sCD14-ST increase in patients without an acute cardiovascular disease. This finding could be underlined by the observation that cTnI values differed less significantly between controls and UAP patients compared to sCD14-ST. In summary, the increase of sCD14-ST concentration in patients without acute cardiovascular diseases or conditions such as, for instance, CHF or angina pectoris, reflects the inflammatory effect in the pathogenesis of atherosclerosis and cardiovascular diseases.

EXAMPLE 5 sCD14-ST Values in Patients with Non ST-Elevation Myocardial Infarction sCD14-ST concentrations were measured using the PATHFAST assay in plasma samples of consecutive patients admitted to the emergency room. Blood sampling was done immediately upon admission. 28 patients with Non-ST-Elevation Myocardial Infarction (NSTEMI) were included.

The results of the sCD14-ST measurements were interpreted with respect to the discharge diagnoses at the subject's discharge, which were independently established during the clinical course of the patients.

TABLE 5 sCD14-ST in patients with NSTEMI (N = 28):

| | |
|---|---|
| Mean | 1001 (95% CI: 640-1361) pg/ml |
| Median | 721 (95% CI: 600-904) |
| Min | 295 pg/ml |
| Max | 4070 pg/ml |
| 25$^{th}$ percentile | 495 (95% CI: 377-656) pg/ml |
| 75$^{th}$ percentile | 984 (95% CI: 841-2434) pg/ml |

The sCD14-ST values measured in plasma samples obtained at admission from patients with NSTEMI at the emergency room are displayed in Tab. 5.

Figure 5:
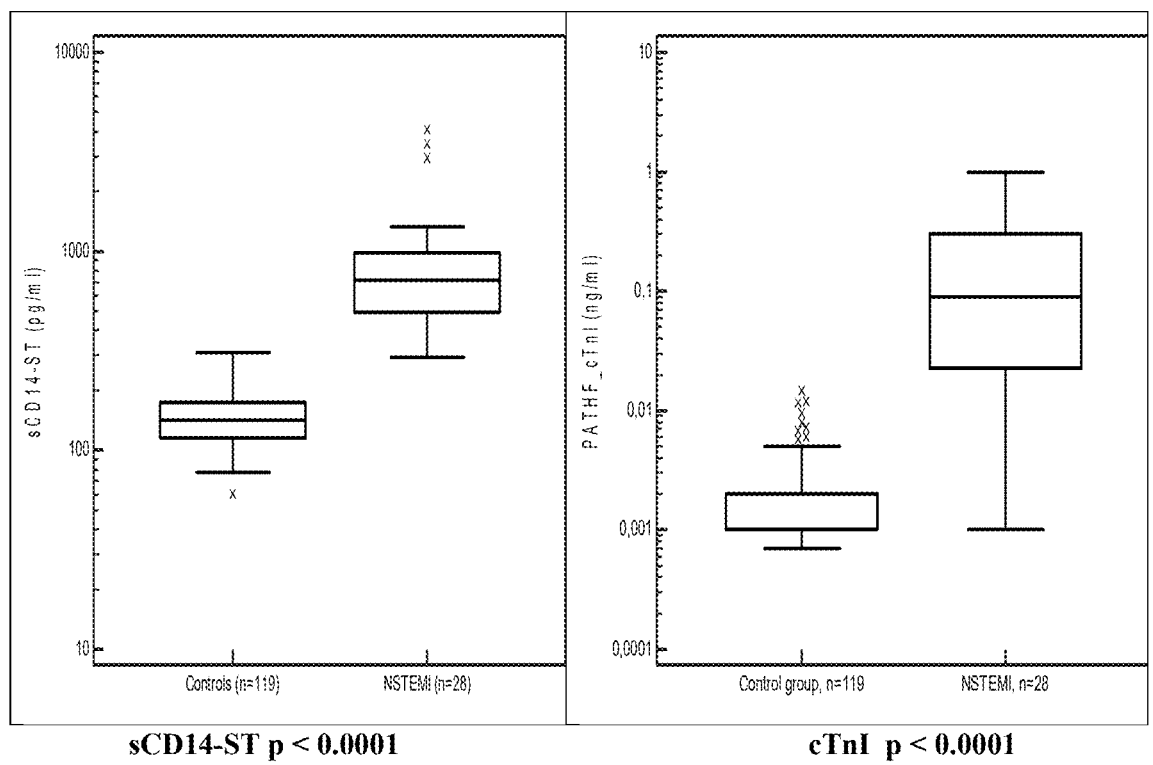
FIG. 5: sCD14-ST and cardiac troponin I (cTnI) values of the healthy control group and subjects with non-ST-elevation myocardial infarction (NSTEMI) at admission to the emergency room.
Figure 6:
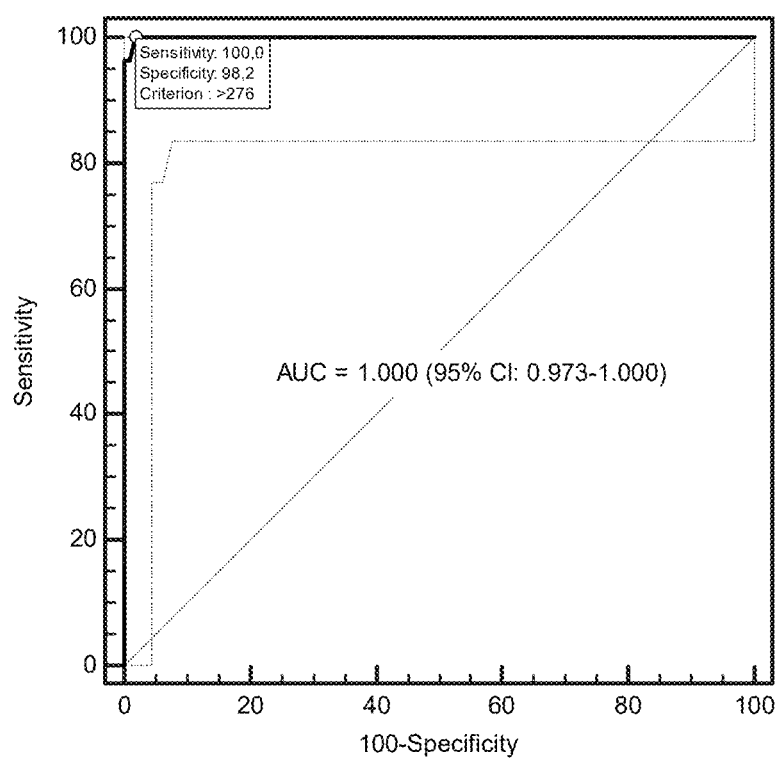
FIG. 6: ROC analyses for the diagnostic validity of sCD14-ST for detecting non-ST-elevation myocardial infarction (NSTEMI) at admission to the emergency room: comparison of AUC curves between the healthy control group and patients presenting at the emergency room with NSTEMI; threshold: sCD14-ST=276 pg/ml; cTnI=0.012 ng/ml.

The difference between healthy controls and patients with NSTEMI was highly significant (p<0.0001) (Tab. 6). cTnI was determined in parallel. Although both markers differed highly significant between the healthy control group and the patients with NSTEMI as displayed in FIG. 5, the comparison of the AUC curves obtained from ROC analysis demonstrated, that sCD14-ST revealed a higher discrimination power (FIG. 6).

Figure 7:
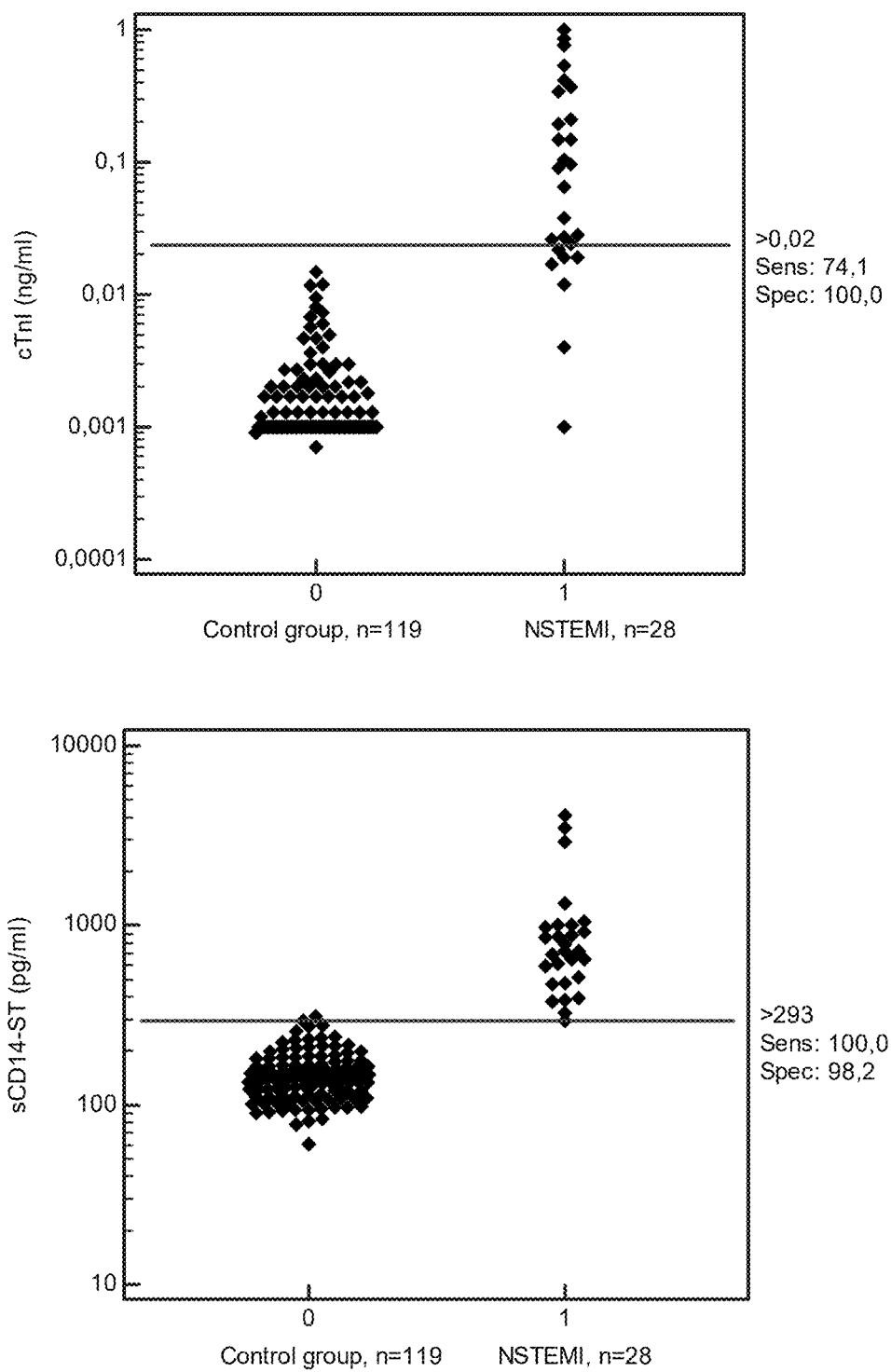
FIG. 7: Comparison of interactive dot diagrams of sCD14-ST (bottom panel) and PATHFAST cTnI (top panel) for the diagnosis of non-ST-elevation myocardial infarction (NSTEMI)

The superior diagnostic accuracy for the diagnosis of NSTEMI in patients presenting with chest pain at the emergency room could be confirmed by including the ROC derived threshold of sCD14-ST and the 99$^{th}$ percentile cutoff of PATHFAST cTnI (0.02 ng/m). The results are displayed in FIG. 7, demonstrating a sensitivity of 100% of sCD14-ST at the cutoff 290 pg/ml whereas PATHFAST cTnI revealed a sensitivity of 74.1% by using the manufacturer recommended cutoff of the 99$^{th}$ percentile concentration of a healthy reference population according to international guidelines. The guidelines recommend cTn determination 3 to 6 hours after admission if the initial measured cTn value is below the cutoff and detection of a rise and/or fall with at least 1 value above the 99th percentile cutoff.

TABLE 6 sCD14-ST values of the healthy control group and patients with NSTEMI

| | Control group | NSTEMI |
|---|---|---|
| Sample size | 112 | 28 |
| Lowest value | 60.1 | 295 |
| Highest value | 311 | 4070 |
| Median | 142.5 | 720.5 |
| 95% CI for the median | 133 to 150 | 600 to 904 |
| Interquartile range | 115 to 174 | 495 to 985 |
| Mann-Whitney test (independent samples) | | |
| Average rank of first group | | 56.5134 |
| Average rank of second group | | 126.4464 |
| Mann-Whitney U | | 1.5 |
| Test statistic Z (corrected for ties) | | 8.161 |
| Two-tailed probability | | P < 0.0001 |

EXAMPLE 6

Diagnosis of Acute Heart Failure sCD14-ST concentrations were determined using the PATHFAST assay in plasma samples obtained from 60 patients admitted to the emergency room with acute dyspnea in whom acute heart failure was assessed by elevated NT-proBNP values exceeding the threshold concentration of 300 pg/ml. All patients revealed NT-proBNP plasma levels 361 pg/ml confirming the diagnosis of acute heart failure (Tab. 7).

TABLE 7 sCD14-ST and NT-proBNP values (pg/ml) in patients with acute heart failure (n = 60)

|  | NT-proBNP | sCD14-ST |
|---|---|---|
| Lowest value | 361 | 345 |
| Highest value | 27287 | 2633 |
| Median | 57746 | 1004 |
| 95% CI for the median | 3821 to 6389 | 789 to 1221 |
| Interquartile range | 2207 to 8488 | 704 to 1498 |

Figure 8:
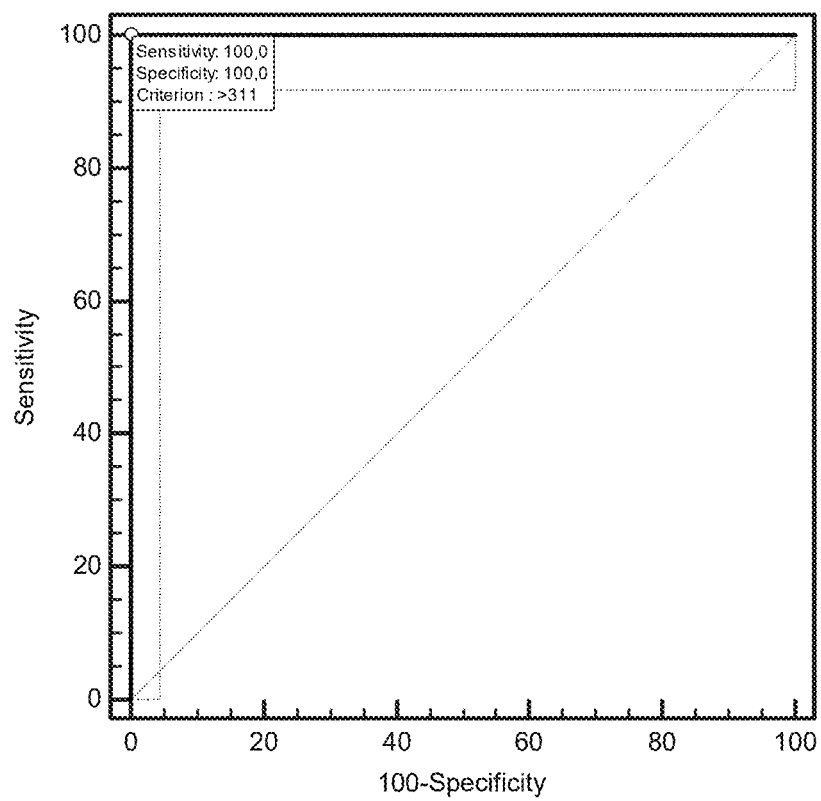
FIG. 8: ROC analyses for the diagnostic validity of sCD14-ST for detecting acute decompensated heart failure (ADHF) in subjects presenting at the emergency room with acute dyspnea; AUC=1.000 (95% CI: 0.976-1.000); SENS=100%, SPEC=100%; threshold=311 pg/ml.

The results of ROC analysis showed that the "rule-in" and "rule-out" of acute heart failure was possible with a sensitivity and a specificity of 100%, respectively, at a sCD14-ST threshold of 311 pg/ml for discrimination between the healthy control group and patients with ADHF (FIG. 8).

Figure 9:
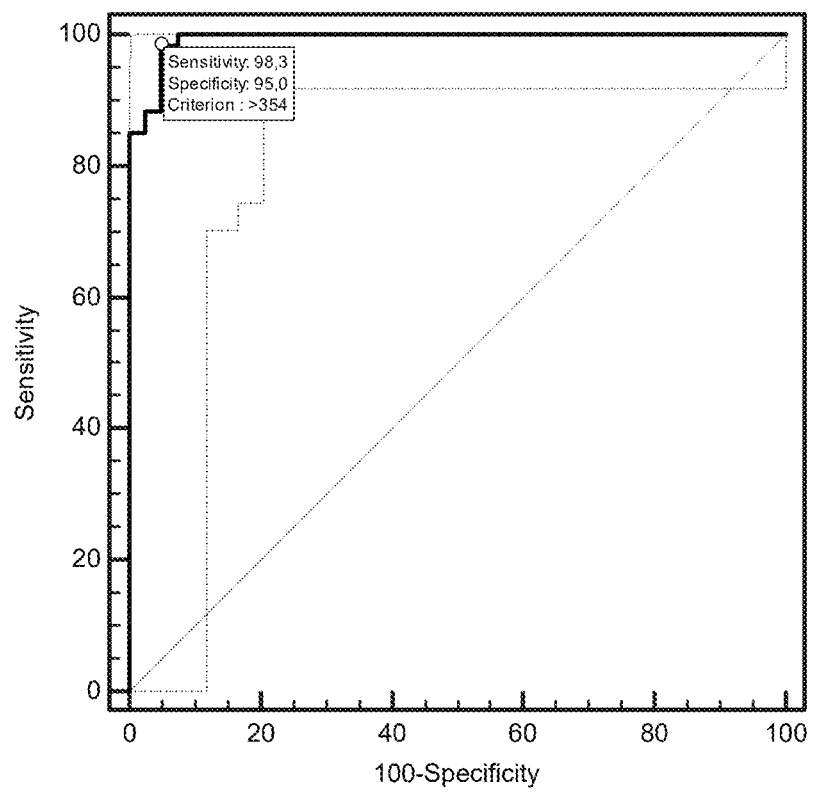
FIG. 9: ROC curve of sCD14-ST for discrimination between acute decompensated heart failure (ADHF) and chronic heart failure (CHF); AUC=0.993 (95% CI: 0.951-1.000); SENS=98.3%, SPEC=95%; threshold=354 pg/ml.

For the discrimination between patients with CHF and patients with acute heart failure the ROC analysis revealed a sensitivity of 98.3% and a specificity of 95.0% at a sCD14-ST threshold of 354 pg/ml and an AUC of 0.993 (FIG. 9)

Figure 10:
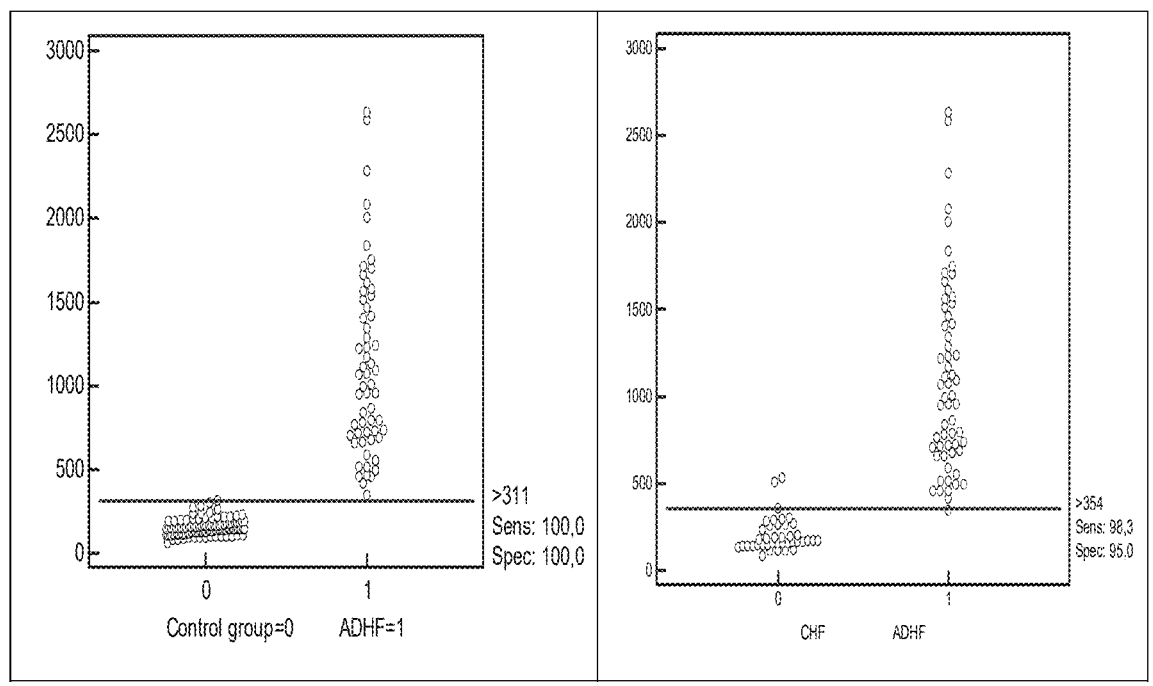
FIG. 10: Comparison of sCD14-ST for discrimination between the healthy control group vs. acute decompensated heart failure (ADHF; threshold 311 pg/ml) and chronic heart failure (CHF) vs. ADHF (threshold 354 pg/ml)
Figure 11:
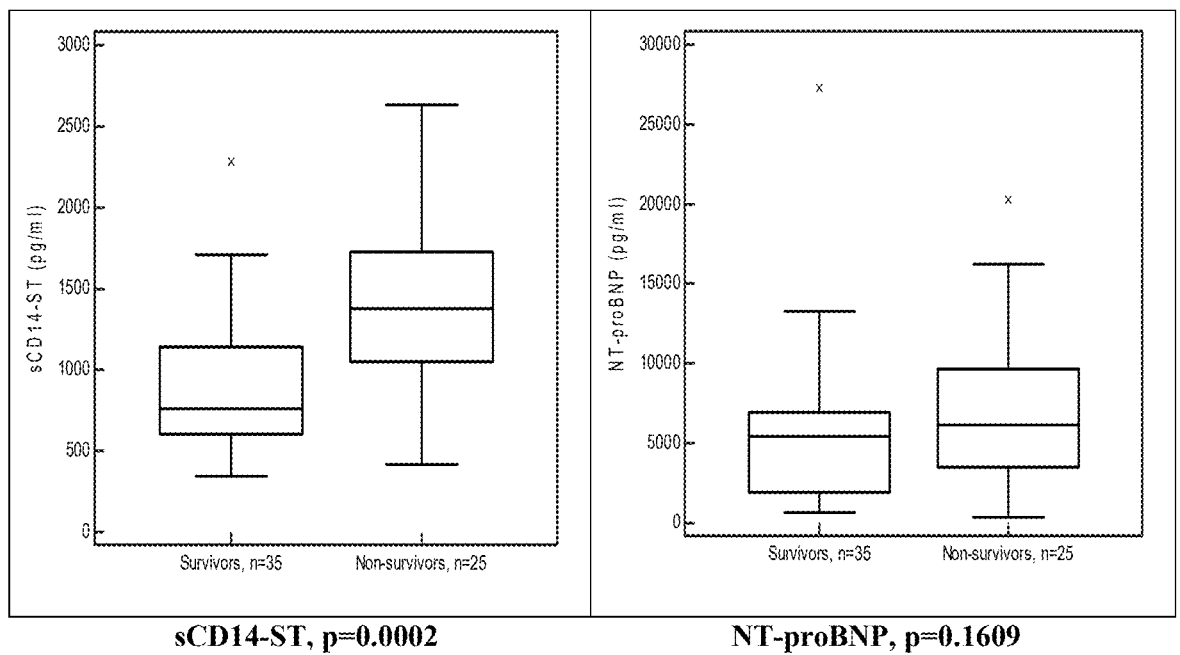
FIG. 11: sCD14-ST values in survivors and non-survivors in comparison with NT-proBNP.
Figure 12:
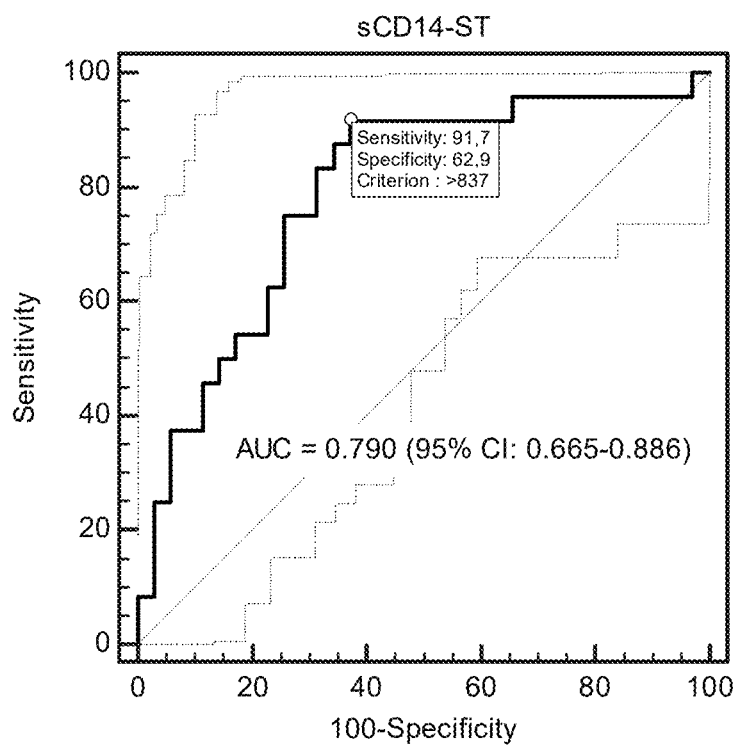
FIG. 12: ROC curve of sCD14-ST for risk of mortality prediction.

These results demonstrated that "rule-in" and "rule-out" of acute heart failure in patients presenting with acute dyspnea at the emergency room is clearly possible using the sCD14-ST plasma concentration (FIG. 10).

EXAMPLE 7

Risk of Mortality Prediction in Patients with Acute Heart Failure 60 patients admitted to the emergency room with acute dyspnea, in whom acute heart failure was assessed by elevated NT-proBNP values exceeding the threshold concentration of 300 pg/ml (Chen A A, et al. NT-proBNP levels, echocardiographic findings, and outcomes in breathless were patients: results from the ProBNP Investigating of Dyspnea in the Emergency Room (PRIDE) echocardiographic substudy. Euer Heart J 2006; 27:839-845), were included in the study. 25 patients died during the 2-year follow-up.

TABLE 8 sCD14-ST values in survivors and non-survivors

|  | Survivors | Non-survivors |
|---|---|---|
| Sample size | 35 | 25 |
| Lowest value | 345 | 414 |
| Highest value | 2284 | 2633 |
| Median | 763 | 1379 |
| 95% CI for the median | 679 to 954 | 1105 to 1671 |
| Interquartile range | 601 to 1144 | 1048 to 1725 |

Mann-Whitney test (independent samples)

| Average rank of first group | 23.0286 |
|---|---|
| Average rank of second group | 40.1667 |
| Mann-Whitney U | 176 |
| Test statistic Z (corrected for ties) | 3.765 |
| Two-tailed probability | P = 0.0002 |

Figure 13:
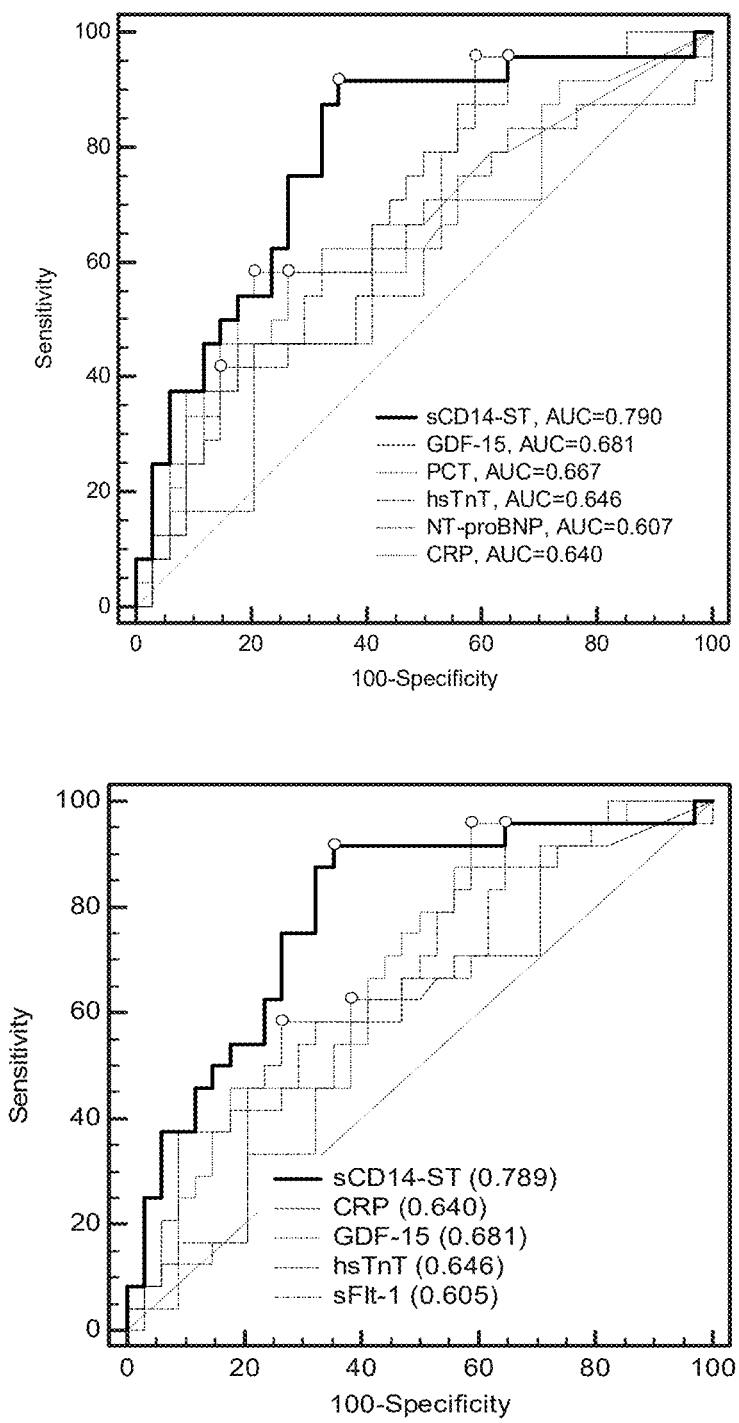
FIG. 13: Comparison of ROC curves for risk of mortality prediction.

Whereas sCD14-ST differed in a highly significant manner between survivors and non-survivors, NT-proBNP values showed no significant difference between the groups. The results of ROC analyses for comparison of the outcome prediction of sCD14-ST with 9 inflammatory and cardiovascular biomarkers, which are already established in routine diagnosis or clinical research revealed superior prognostic validity of sCD14-ST in patients with acute heart failure (FIG. 13).

EXAMPLE 8

Risk of Mortality Prediction in Patients After Elective Cardiac Surgery sCD14-ST and NT-proBNP concentration were measured in EDTA plasma samples obtained at the first postoperative day from 49 patients undergoing elective cardiac surgery. 24 patients died during 2-year follow-up.

TABLE 9 sCD14-ST values in survivors and non-survivors

|  | Survivors | Non-survivors |
|---|---|---|
| Sample size | 25 | 24 |
| Lowest value | 103 | 401 |
| Highest value | 1926 | 7438 |
| Median | 248 | 1230 |
| 95% CI for the median | 190 to 305 | 936 to 1879 |
| Interquartile range | 180 to 308 | 832 to 2024 |

Mann-Whitney Test (Independent Samples)

| Average rank of first group | 14.0 |
|---|---|
| Average rank of second group | 36.4 |
| Mann-Whitney U | 26.0 |
| Test statistic Z (corrected for ties) | 5.5 |
| Two-tailed probability | P < 0.0001 |

Figure 14:
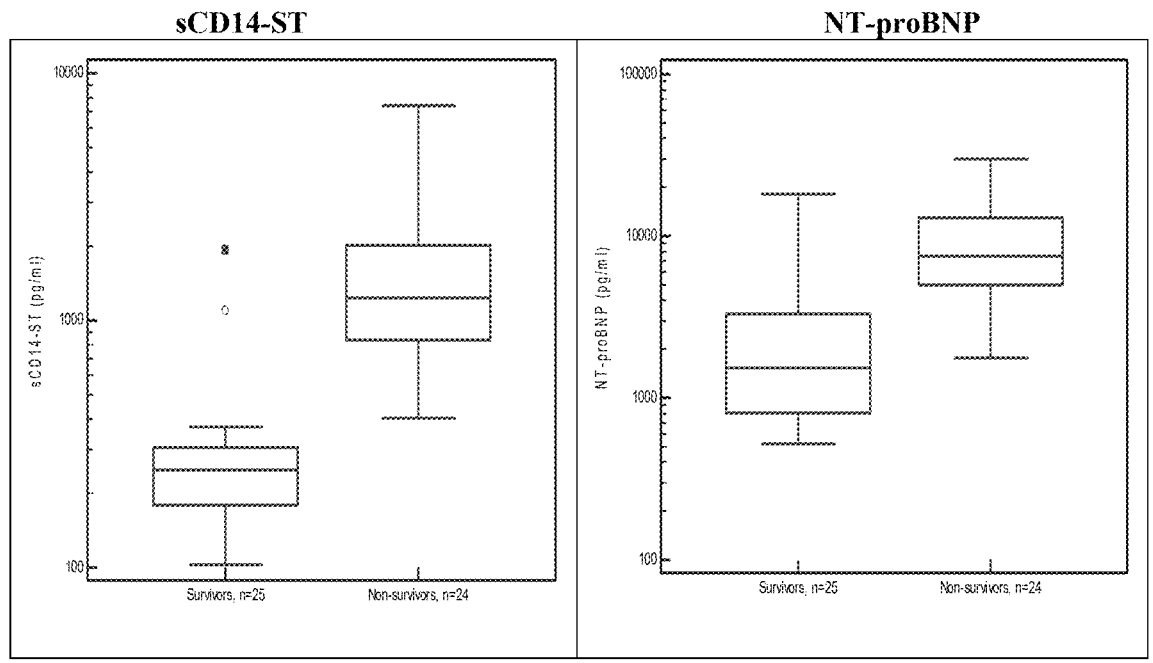
FIG. 14: sCD14-ST values in survivors and non-survivors in comparison with NT-proBNP

NT-proBNP:

| Average rank of first group | 15.5 |
|---|---|
| Average rank of second group | 34.9 |
| Mann-Whitney U | 63.0 |
| Large sample test statistic Z | 4.7 |
| Two-tailed probability | P < 0.0001 | sCD14-ST and NT-proBNP differed highly significantly between survivors and non-survivors but NT-proBNP showed only a minor difference between the groups (FIG. 14).

Figure 15:
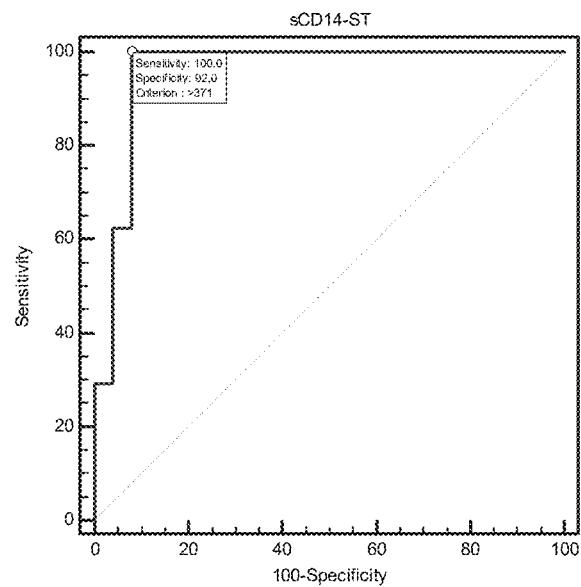
FIG. 15: ROC curve of sCD14-ST for risk of mortality prediction after elective heart surgery
Figure 16:
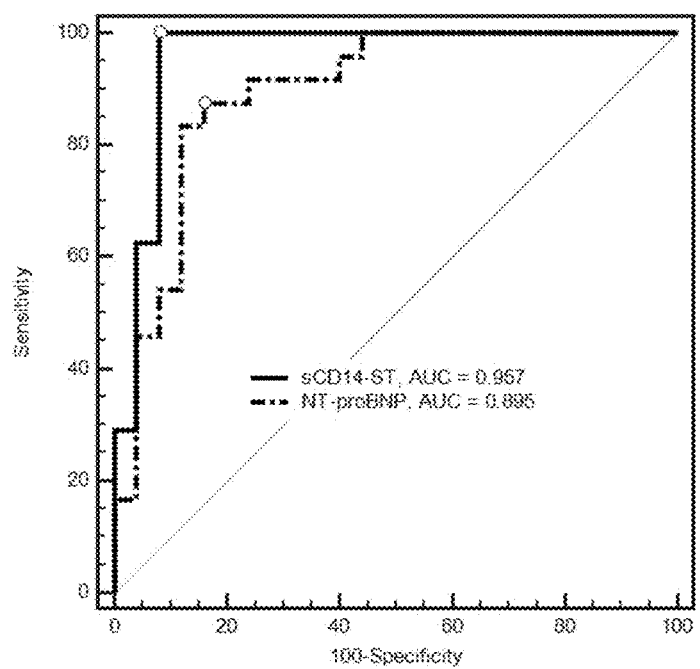
FIG. 16: Comparison of ROC curves for risk of mortality prediction after elective heart surgery.

The results of ROC analyses for comparison of sCD14-ST (AUC=0.957, cutoff 371 pg/ml, sensitivity 100%, specificity=92.0%) with NT-proBNP (AUC=0.895, cutoff=4249 pg/ml, sensitivity 87.5%, specificity 84.0%) for outcome prediction revealed superior prognostic validity of sCD14-ST in patients undergoing elective cardiac surgery (FIGS. 15 and 16).

EXAMPLE 9

Differentiation Between Cardiac and Non-Cardiac Chest Pain at Admission

Objective and Methods 30 patients with chest pain suspicious for acute myocardial infarction (AMI) admitted to the emergency room were included in the study. Troponin was initially negative. AMI, acute coronary syndrome (ACS), or unstable angina pectoris (UAP) were excluded by standard diagnostic procedures according to current guidelines including serial troponin measurement, electrocardiography (ECG) and further care for confirmation of the non-cardiac origin of the initial chest pain symptoms. sCD14-ST was determined at admission and compared with sCD14-ST values measured at admission in a group of 17 patients with cardiac chest pain but without AMI in whom the final diagnosis UAP was established.

Results

Figure 17:
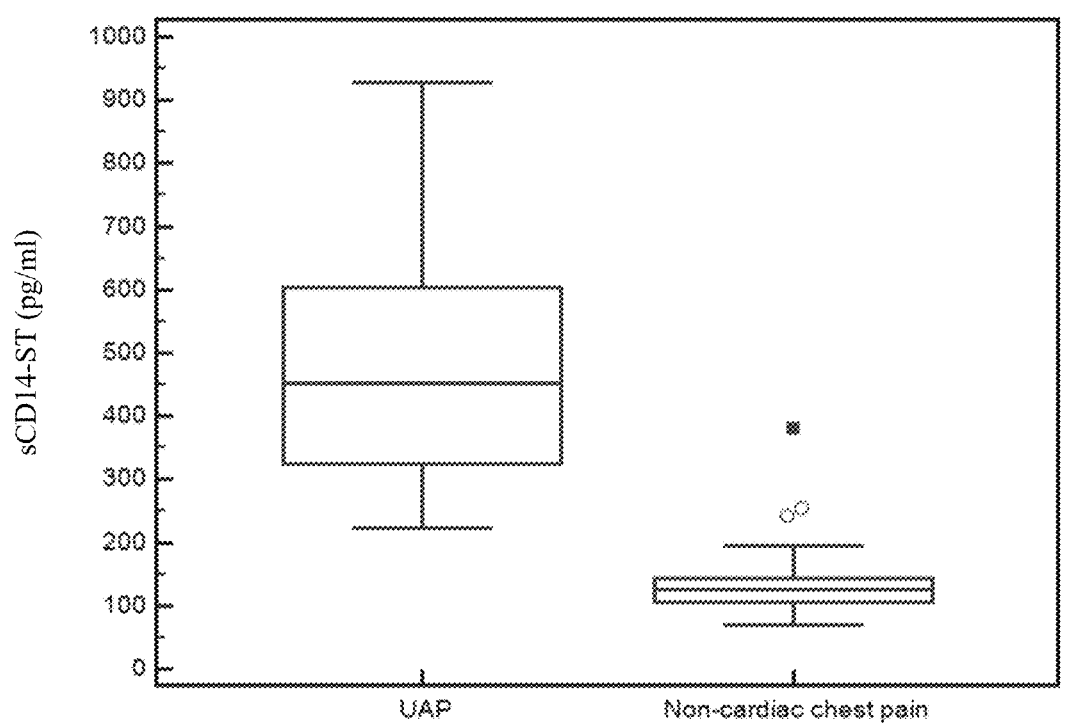
FIG. 17: sCD14-ST in unstable angina pectoris (UAP) and patients with non-cardiac chest pain

The patient group with UAP and initially cardiac chest pain showed significantly higher sCD14-ST values compared to the patient group with non-cardiac chest pain (p<0.0001; Tab. 9, FIG. 17).

TABLE 9 sCD14-ST concentration in patients with cardiac and non-cardiac chest pain at admission to the emergency room

| Sample 1 | |
|---|---|
| Variable | sCD14_ST |
| Select | UAP |

| Sample 2 | |
|---|---|
| Variable | sCD14_ST |
| Select | Non-cardiac chest pain |

| | UAP | Non-cardiac chest pain |
|---|---|---|
| Sample size | 17 | 30 |
| Lowest value | 223 | 69 |
| Highest value | 928 | 381 |
| Median | 452 | 125 |
| 95% CI for the median | 333 to 602 | 110 to 142 |
| Interquartile range | 324 to 604 | 105 to 144 |

| Mann-Whitney test (independent samples) | |
|---|---|
| Average rank of first group | 33.5294 |
| Average rank of second group | 13.3200 |
| Mann-Whitney U | 8.00 |
| Test statistic Z (corrected for ties) | 5.240 |
| Two-tailed probability | P < 0.0001 |

Figure 18:
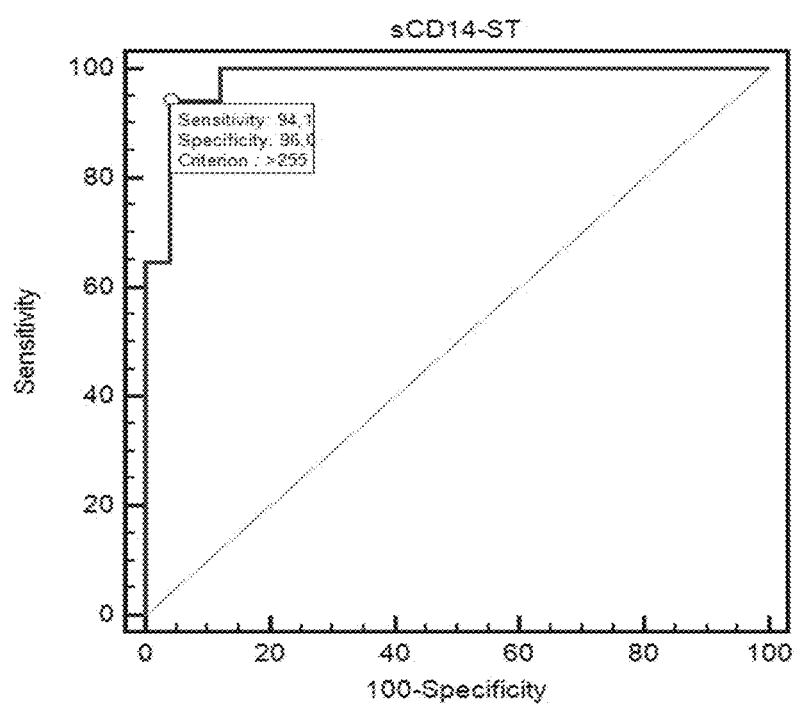
FIG. 18: ROC curve of sCD14-ST for discrimination between cardiac and non-cardiac chest pain

Receiver Operator Characteristic (ROC) analysis for discrimination between cardiac and non-cardiac chest pain revealed an AUC value of 0.981 with a corresponding sensitivity of 94.1% and specificity of 96.0% (see FIG. 18).

Conclusion

The results of the ROC analysis demonstrated a high discriminatory power of sCD14-ST for discrimination between cardiac and non-cardiac chest pain. The ROC derived cutoff value was 255 pg/ml and in accordance with the other thresholds of sCD14-ST established in the diagnosis of cardiac diseases.

The results show that chest pain patients with sCD14-ST values below the cutoff of 255 pg/ml could be assigned to patients with non-cardiac chest pain and discharged from the emergency room without further diagnostic procedure, e.g. serial troponin measurement, ECG or further care.

EXAMPLE 10 sCD40 and sCD40-ST as Cardiac Markers for Risk of Mortality Prediction in Patients with Acute Heart Failure (AHF)

Methods sCD14 and sCD14-ST concentrations were measured in base-line plasma samples obtained from 35 patients (32 to 89 years old, median 67 years; 13 females, 22 males) attending the emergency department. Diagnosis of acute heart failure (AHF) was confirmed by NT-proBNP determination using an NT-proBNP cutoff-value of 300 ng/L according to the PRIDE study (Januzzi J et al.: The N-terminal Pro-BNP investigation of dyspnea in the emergency department (PRIDE) study. Am J Cardiol 2005; 95:948-54). Outcome measure was mortality within 28 days. sCD14 was measured using the Quantikine Human sCD14 Immunoassay (R&D Systems Inc. Minneapolis, MN, USA). sCD14-ST was determined using the PATHFAST Presepsin assay (Mitsubishi Chemical Medience). NT-proBNP was measured using the ELECSYS proBNP assay (Roche Diagnostics).

Results

Figure 19:
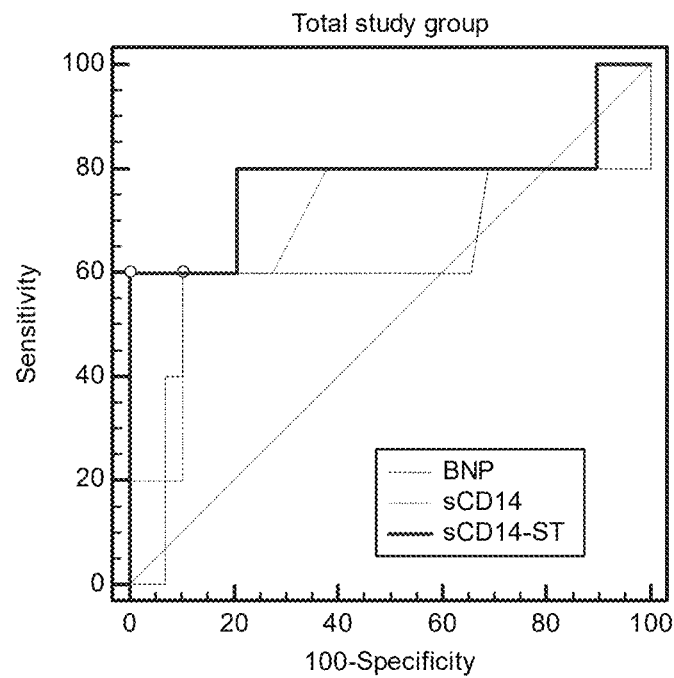
FIG. 19: Comparison of ROC curves for mortality prediction by sCD14-ST and sCD14 levels in (A) total study group and (B) patients with acute heart failure (AHF).
Figure 19:
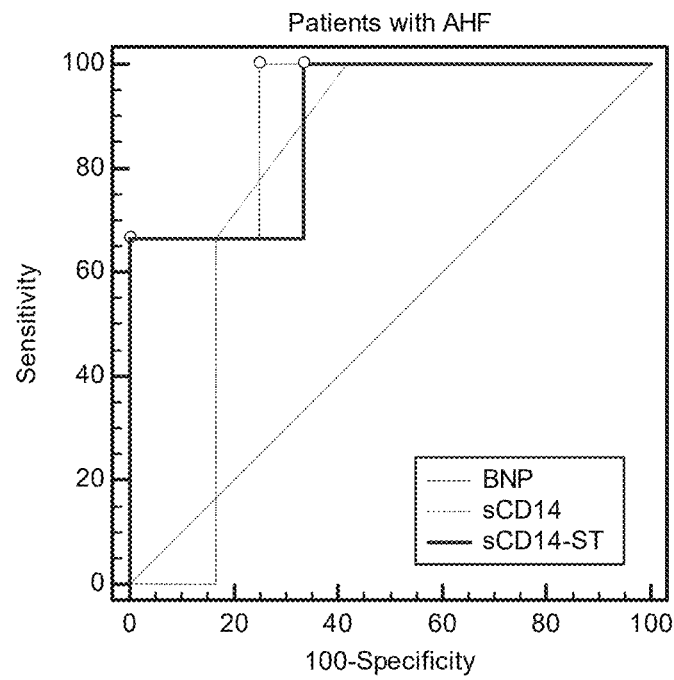
Figure 20:
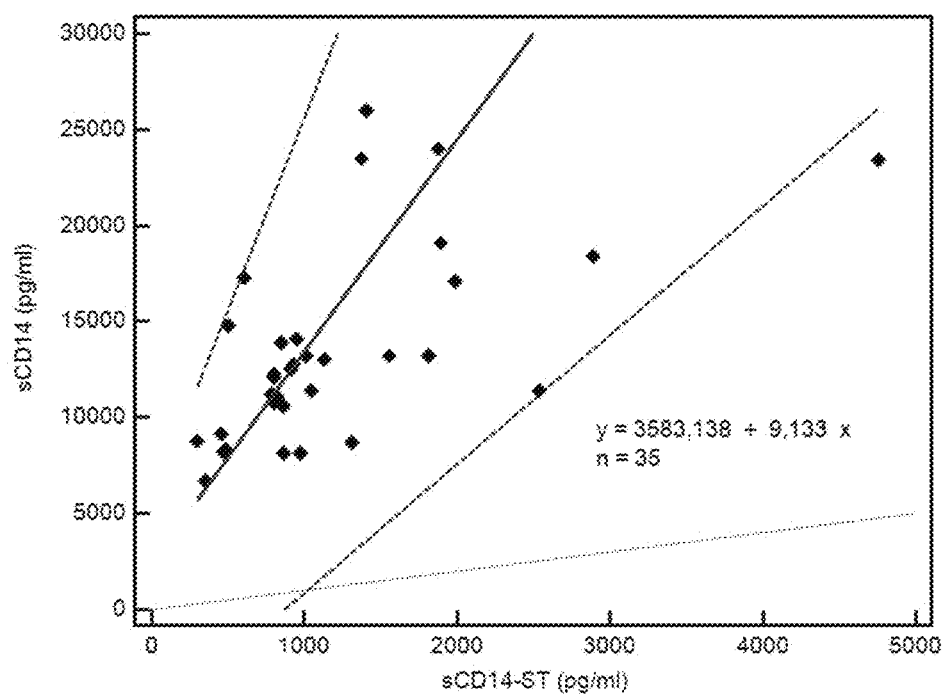
FIG. 20: Method comparison of sCD14-ST and sCD14 in cardiac disease: a Bablok—Passing regression analysis shows sufficient correlation for sCD40 and sCD14-ST (mortality prediction in patients with acute heart failure, AHF)
Figure 21:
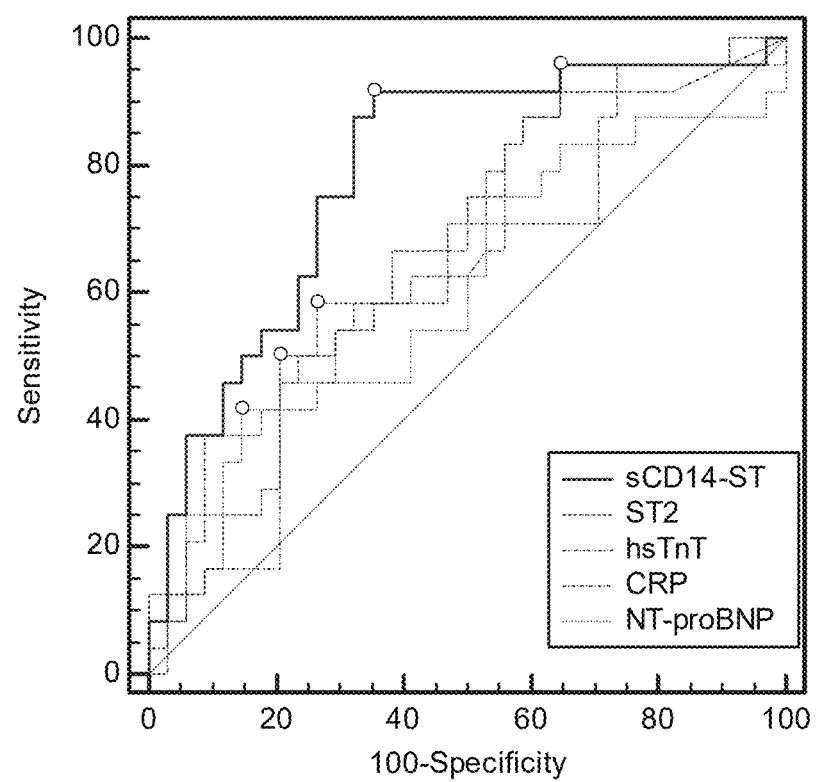
FIG. 21 Combination of sCD14-ST with additional markers: ROC curves for discrimination between survivors and non-survivors

The baseline concentrations of the study group ranged from 17-2264 ng/L, median=208 ng/L, 6677-26000 ng/L, median=12800 ng/L, and 300-8893 ng/L, median 952 ng/L for NT-proBNP, sCD14, and sCD14-ST, respectively. 15 patients revealed NT-proBNP values above the cutoff-level 300 ng/L confirming the diagnosis of AHF. During the 28-days follow up 5 patients of the total study group (14.3%) and 3 patients of the AHF group (20.0%) died. The area under the curves (AUCs) obtained from the ROC analysis for discrimination between survivors and non-survivors of the total study group and of the AHF group are displayed in Tab. 10, and the ROC curves are shown in FIG. 19 (panel (A): total study group; panel (B): AHF group). Although the concentration of sCD14 was found to be approx. 10 times higher compared to sCD14-ST both markers showed sufficient correlation as demonstrated by Bablok—Passing regression (FIG. 20). The ROC-AUCs for sCD40, sCD14-ST and NT-proBNP showed significantly higher discriminatory power between survivors and non-survivors of the AHF group than of the total study group (Tab. 10, FIG. 19).

TABLE 10

Results of the ROC analysis

| | Total study group | | Patients with AHF | |
|---|---|---|---|---|
| | AUC | 95% CI | AUC | 95% CI |
| BNP | 0.6 | 0.44-0.78 | 0.8 | 0.53-0.96 |
| sCD14 | 0.7 | 0.53-0.86 | 0.9 | 0.64-0.99 |
| sCD14_ST | 0.8 | 0.60-0.90 | 0.9 | 0.62-0.99 |

Conclusion sCD14 and sCD14-ST revealed superior results from ROC analysis for risk of mortality prediction in patients with acute heart failure compared to the already established cardiac marker NT-proBNP demonstrating that sCD14 and sCD14-ST could be used as cardiac markers.

EXAMPLE 11

Multi-Marker Approach for Risk Stratification of Patients with Acute Heart Failure (AHF)

This study demonstrates the additional diagnostic and prognostic value of simultaneous assessment of sCD14-ST in combination with additional markers. In patients with acute heart failure, sCD14-ST was assessed in pairwise combination with:

a marker of the interleukin-1 receptor family (ST2—Plasma concentrations of soluble ST2 are increased in inflammatory diseases and in heart diseases, especially in acute heart failure), a neurohormonal marker (NT-proBNP), an ischemic cardiac marker (high-sensitivity cTnT, i.e. hsTnT), or an inflammatory marker (CRP).

Methods: Marker concentrations were measured in baseline plasma samples obtained from 60 patients (50 to 90 years old, median 77 years; 26 females, 34 males) with acute heart failure attending the emergency department. Patients with myocardial infarction or sepsis were excluded. Outcome measure was mortality at 2 years. ST2 was measured using the Presage ST2 assay (Critical Diagnostics, San Diego, CA, USA). sCD14-ST was determined using the PATHFAST Presepsin assay (Mitsubishi Chemical Medience). Amino-terminal pro B-type natriuretic peptide (NT-proBNP), high-sensitivity cardiac troponin T (hscTnT) and C-reactive protein (CRP) were measured using the ELECSYS tests (Roche Diagnostics).

Results: The baseline NT-proBNP concentrations of the study group ranged from 361-27287 ng/L, median (IQR)=5773 (2207-8488) ng/L confirming the diagnosis of acute heart failure. During the 2-year follow-up period, 25 patients (41.7%) died. The results of Mann-Whitney independent sample test and ROC-analysis for discrimination between survivors and non-survivors are summarized in Tab. 11.

Tab. 12 contains the results of ROC analysis and Net Reclassification for the combination of the markers ST2, CRP, hsTnT and NT-proBNP with sCD14-ST. The simultaneous assessment of the marker combinations enhanced the prognostic validity as shown by increasing of the AUC values and the Net Reclassification Index.

TABLE 11

Prognostic validity criteria for mortality prediction in AHF

| | Survivors, n = 35<br>Median (IQR) | Non-survivors, n = 25<br>Median (IQR) | p-value | AUC<br>(ROC analysis) |
|---|---|---|---|---|
| sCD14-ST, ng/L | 763 (601-1144) | 1414 (1069-1712) | 0.0001 | 0.794 |
| ST2, µg/L | 57 (34-83) | 79 (56-99) | 0.0351 | 0.661 |
| CRP, g/L | 13 (3.8-25.3) | 25.6 (8.2-62.5) | 0.0704 | 0.640 |
| hscTnT, µg/L | 21 (12-33) | 31 (20-47) | 0.0280 | 0.646 |
| NT-proBNP, ng/L | 5453 (1901-6919) | 6161 (3518-9664) | 0.1609 | 0.607 |

TABLE 12

Risk of mortality prediction using combination of markers with sCD14-ST

| Marker | AUC<br>alone | AUC<br>combination | AUC<br>Difference | Net Reclassification<br>% correct classified |
|---|---|---|---|---|
| ST2 | 0.661 | 0.806 | 0.145 | 73.33 |
| CRP | 0.640 | 0.808 | 0.168 | 68.97 |
| hscTnT | 0.646 | 0.808 | 0.162 | 71.67 |
| NT-proBNP | 0.607 | 0.803 | 0.196 | 73.33 |

Conclusion: The simultaneous assessment of sCD14-ST and ST2, sCD14-ST and a NT-proBNP, sCD14-ST and hsTnT, or sCD14-ST and CRP in patients with acute heart failure improves the risk of mortality prediction compared the determination of the markers alone.

---

The invention claimed is:

1. A method of diagnosing and treating a cardiovascular disease or condition in a patient, said method comprising:
   a. obtaining a blood, plasma, or serum sample from a human patient;
   b. detecting sCD14-ST present in the blood, plasma, or serum sample, or having sCD14-ST detected in the blood, plasma, or serum sample;
   c. diagnosing the patient with a cardiovascular disease or condition when the presence of sCD14-ST in the blood, plasma, or serum sample is detected; and
   d. administering an appropriate treatment to the diagnosed patient, wherein an amount of sCD14-ST in the diagnosed patient to be administered is 345 pg/ml or higher, and wherein the appropriate treatment is selected from the group consisting of antibiotics, probiotics, and lactulose;
   wherein the patient shows symptoms of one or more cardiovascular diseases or conditions selected from the group consisting of chronic heart failure and angina pectoris; and
   wherein the sCD14-ST has an apparent molecular weight of 13±2 kDa when electrophoresed under non-reducing conditions.

2. The method according to claim 1, wherein the method is a method for determining whether the patient needs to be hospitalized due to chronic heart failure or angina pectoris.

3. The method according to claim 1, wherein the method is for identifying a subject having chronic heart failure or angina pectoris that has an elevated risk of mortality, wherein the amount of sCD14-ST is 500 pg/ml or higher.

4. A method of treating a cardiovascular disease or condition in a patient, said method comprising:
   a. obtaining a blood, plasma, or serum sample from a human patient;
   b. detecting sCD14-ST present in the blood, plasma, or serum sample, or having sCD14-ST detected in the blood, plasma, or serum sample; and
   c. administering an appropriate treatment to a patient showing an amount of sCD14-ST of 345 pg/ml or higher, and wherein the appropriate treatment is selected from the group consisting of antibiotics, probiotics, and lactulose;
   wherein the patient shows symptoms of one or more cardiovascular diseases or conditions selected from the group consisting of chronic heart failure and angina pectoris, and
   wherein the sCD14-ST has an apparent molecular weight of 13±2 kDa when electrophoresed under non-reducing conditions.

* * * * *